United States Patent
Shaw

(10) Patent No.: US 10,214,578 B1
(45) Date of Patent: Feb. 26, 2019

(54) VARIANTS OF IGG-FC FUSION THAT PROVIDE FOR SITE-SPECIFIC CONJUGATION AT THE N-TERMINUS

(71) Applicant: Gray D Shaw, Half Moon Bay, CA (US)

(72) Inventor: Gray D Shaw, Half Moon Bay, CA (US)

( * ) Notice: Subject to any disclaimer, the term of this patent is extended or adjusted under 35 U.S.C. 154(b) by 0 days.

(21) Appl. No.: 15/215,051

(22) Filed: Jul. 20, 2016

Related U.S. Application Data

(60) Provisional application No. 62/195,812, filed on Jul. 23, 2015, provisional application No. 62/194,806, filed on Jul. 20, 2015.

(51) Int. Cl.
*C07K 14/70* (2006.01)
*C07K 14/705* (2006.01)
*C07K 7/08* (2006.01)
*C07K 17/00* (2006.01)

(52) U.S. Cl.
CPC .......... *C07K 14/70596* (2013.01); *C07K 7/08* (2013.01); *C07K 17/00* (2013.01); *C07K 2319/30* (2013.01); *C07K 2319/33* (2013.01)

(58) Field of Classification Search
None
See application file for complete search history.

(56) References Cited

PUBLICATIONS

Baudino et al. (Journal of Immunology, 181: 4107-4112, 2008).*

* cited by examiner

*Primary Examiner* — Nelson B Moseley, II
(74) *Attorney, Agent, or Firm* — Steven R. Lazar

(57) ABSTRACT

Conjugated lysine-depleted variants of fragment crystallizable (Fc) regions of immunoglobulins are disclosed. Also disclosed are fusion proteins comprised of C-terminal targeting peptide sequences, fused to such lysine-depleted variant IgG-Fc domains. Polynucleotides encoding such proteins, compositions and kits containing such proteins, and methods of using such proteins are also disclosed.

16 Claims, 7 Drawing Sheets
Specification includes a Sequence Listing.

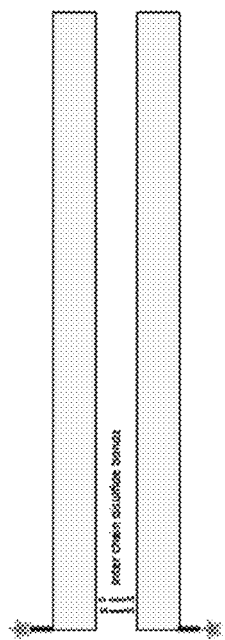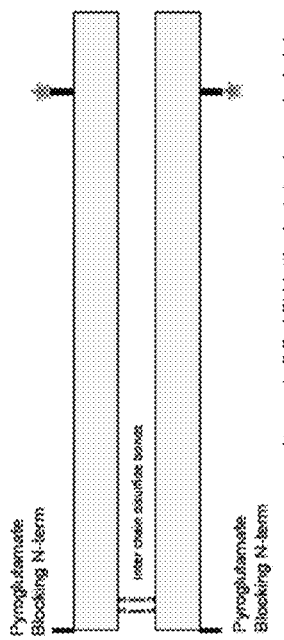
Fig 1
FIG. 1A
FIG. 1B

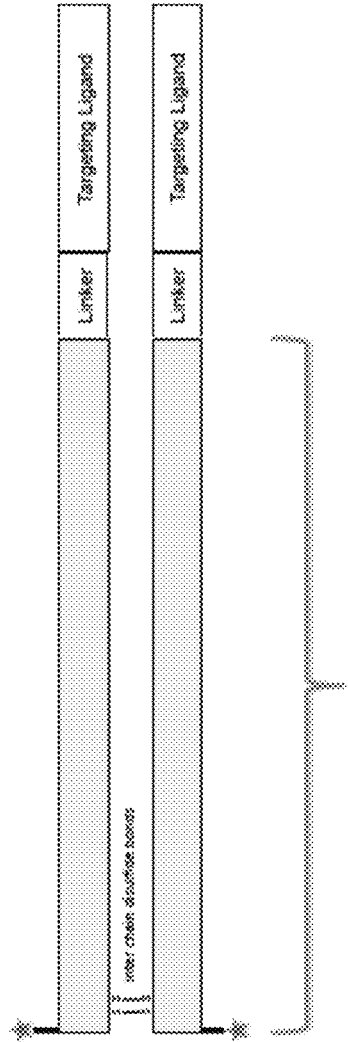
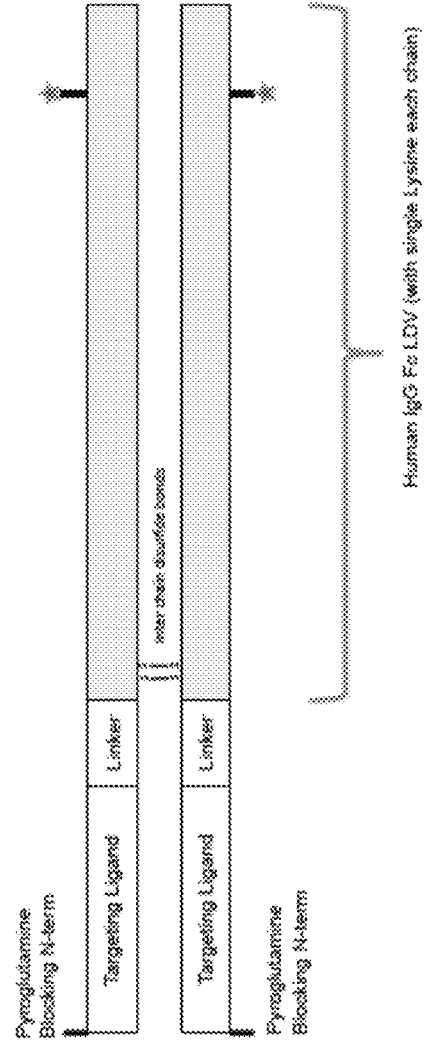
Fig. 2
FIG 2A
FIG 2B

Fig 3

IgG1 Fc (Kabat Numbering)

```
221        231        241    248 251        261
DKTHTCPPCP APELLGGPSV FLFPPKPKDT LMISRTPEVT CVVVDVSHED
271        281        291        301        311
PEVKFNWYVD GVEVHNAKTK PREEQYNSTY RVVSVLTVLH QDWLNGKEYK
321        331    338 341        351        361
CKVSNKALPA PIEKTISKAK GQPREPQVYT LPPSRDELTK NQVSLTCLVK
371        381        391        401        411
GFYPSDIAVE WESNGQPENN YKTTPPVLDS DGSFFLYSKL TVDKSRWQQG
421        431        441    447
NVFSCSVMHE ALHNHYTQKS LSLSPGK
```

Fig 4 kDa
250
150
100
75
50
37
25
20
15
10

Recombinant LDV-Fc purified with protein A ( SDS-PAGE, reducing conditions, coomasie staining).

VARIANTS OF IGG-FC FUSION THAT PROVIDE FOR SITE-SPECIFIC CONJUGATION AT THE N-TERMINUS

TECHNICAL FIELD

The present invention relates to the immunoglobulin G fragment crystallizable regions (IgG Fc), altered such that homogeneous, site-specific amine conjugations can be achieved. Also provided are design and production of such engineered Fc regions, and use of such regions in targeted peptide fusion proteins.

BACKGROUND OF THE INVENTION

The immunoglobulin G fragment crystallizable region (IgG-Fc) can be used as a scaffold to attach drugs and polymers. However, when chemical attachment to their amine groups is attempted, a heterogeneous mixture of attachments results, which is undesirable for therapeutic or diagnostic use. (Panowski et al., mAbs, 6:34-45 (2014).

IgG-Fc domains are commonly used in the art to create IgG-Fc fusions with a variety of polypeptides (Czajkowsky et al., EMBO Mol Med, 4:1015-1028 (2012)). In some cases, the polypeptide to be fused may be devoid of lysine residues. In such cases, only the primary amine group of the polypeptide at the N-terminus of the fusion polypeptide represents a unique attachment site. Alternatively, the primary amine group at the N-terminus may be eliminated if the N-terminal amino acid is glutamine or glutamate and is subsequently converted to pyroglutamate. (Lui et al., J. Biol. Chem, 286:11211-11217 (2011)). As early as 2007, over two dozen monoclonal antibodies and Fc fusion proteins had been approved as therapeutic products, including blockbuster products such as Rituxan® (Genentech; Biogen-Idec), Remicade® (Centocor), Herceptin® (Genentech), Avastin® (Genentech), Bexxar® (Glaxo SmithKline), Tysabri® (Biogen-Idec), Humira® (Abbott), Enbrel® (Amgen); and Campath® (Takeda-Millennium).

The Fc portion of human IgG1 contains 20 native lysine residues, resulting in a total of 40 lysines present in the functional dimeric Fc. Chemical conjugation, using amine reactive chemistries results in heterogenous attachments at these naturally occurring lysines. Moreover, several of the native lysines near and within the CH2-CH3 interface may contribute to the binding interaction with protein A. For example, lysine 338 (by Kabat EU numbering) that is conserved in several species of IgG has been identified as a critical residue for the binding of IgG to Staphylococcal protein A (hereafter referred to as "protein A") (Deisenhofer (1981) Biochemistry, 20:2361-2370; Nagaoka and Akaike (2003), Protein Engineering (2003) 16:243-5). The disclosures of the above documents are hereby incorporated by reference.

U.S. Pat. No. 8,889,629 discloses fusion molecules comprising two or more PSGL-1 domains fused to an IgG-Fc domain.

BRIEF SUMMARY OF THE INVENTION

The present invention involves extensive engineering the Fc portion of immunoglobulins (IgG Fc) to remove most or all of the amine groups such that the number and position of remaining amine reactive groups is limited to enable site-specific chemical conjugations. These lysine-depleted variants (LDV) of IgG Fc molecules still retain certain characteristic IgG Fc functions.

The Fc portion of human IgG1 contains 20 native lysine residues. These lysine residues are located at positions 222, 246, 248, 274, 288, 290, 317, 320, 322, 326, 334, 338, 340, 360, 370, 392, 409, 414, 439 and 447 according to the Kabat EU numbering system (see FIG. 3). Chemical conjugation, using amine reactive chemistries, results in heterogenous attachments at these naturally occurring lysines. Moreover, several of the native lysines near and within the CH2-CH3 interface have been reported to contribute to the binding interaction with protein A. For example, lysine 338 (by Kabat EU numbering) that is conserved in several species of IgG has been identified as a critical residue for the binding of IgG to Staphylococcal protein A (hereafter referred to as "protein A") (Deisenhofer, J., Biochemistry (1981); Nagaoka and Akaike (2003), Protein Engineering 16:243-245). Lysine 246 has also been reported to be a proximal residue to protein A, and therefore, an important potential contributor for protein A binding. Additionally, the lysine 248 residue has been reported to be involved in Fc interfacing with protein G, another protein that is useful for purification of human IgG Fc domain (Sauer-Eriksson et al. (1995) Structure 3:265-278). The disclosure of the above documents are hereby incorporated by reference.

The binding of the lysine 338 residue of IgG-Fc has been particularly useful for scale-up of commercial production of IgG-Fc containing peptides using protein A chromatography for purification. Based upon the ability of protein A to selectively bind to the IgG-Fc domain, protein A chromatography is widely used in laboratories and industry to purify a desired IgG-Fc containing peptide. For example, a desired IgG-Fc containing peptide can be purified from a composition, i.e., separated from undesired materials, including other peptides, such as host cell proteins, that may be present in a composition produced from recombinant host cells engineered to produce such desired IgG-Fc containing peptide, utilizing the ability of protein A to bind to IgG-Fc.

The present invention comprises IgG-Fc variant molecules in which the lysine 338 residue that was previously believed critical to the ability of IgG to bind protein A has been replaced with another amino acid residue. The present invention further comprises IgG-Fc variant molecules in which one or more additional lysine (K) residues have been replaced by a different amino acid residue, such as alanine (A), arginine (R) or glutamine (Q). In a particular aspect, the present invention comprises IgG Fc variant molecules in which alternative amino acids are substituted for each of the 19 native lysine residues. Surprisingly, despite these many substitutions, lysine depleted IgG Fc variant molecules are secreted from mammalian cells at levels comparable to that of normal IgG Fc. Moreover, as shown by SD S-PAGE analysis in FIG. 4, the secreted recombinant lysine-depleted IgG Fc molecule (hereafter termed "LDV Fc") retains the capacity to form dimers. Remarkably, as shown in FIG. 4, LDV Fc retains the ability to bind to protein A with high affinity. These results indicate that LDV Fc molecules, with the replacement of all 19 native lysine residues, can retain a similar structural integrity as compared with the normal native Fc molecule. This was an unexpected finding in light of the previously held belief that certain of the lysine residues, in particular lysine residue 338, was critical to protein A binding.

In certain embodiments, the present invention comprises an LDV Fc molecule that is capable of binding to protein A and/or protein G, wherein all lysine residues within the Fc domain have been replaced by other amino acids, for example, alanine, arginine or glutamine, and which has a unique reactive amine group at its N-terminus. In these embodiments, the LDV Fc molecule comprises only a single amine, at the N-terminus. In other embodiments, the present invention comprises an LDV Fc molecule that is capable of binding to protein A and/or protein G, wherein all lysine residues within the Fc domain have been replaced by other amino acids and has a pyroglutamate residue at its N-terminus. In these embodiments, the LDV Fc molecule is devoid of all amine groups.

In other embodiments, the present invention comprises an LDV Fc molecule that is capable of binding to protein A and/or protein G, wherein said LDV Fc molecule comprises a single lysine residue within the Fc domain and has a pyroglutamate residue at its N-terminus. In particular examples of this embodiment, the single lysine residue is retained at position 392 or 414 within the Fc domain. Alternatively, the lysine residue may be retained at a position selected from: 222, 246, 248, 274, 288, 290, 317, 320, 322, 326, 334, 340, 360, 370, 392, 409, 414, 439 or 447. The single lysine residue may also be located at a non-native position, such as residues: 358, 362, 364, 398, 416, 422 or 446. In other embodiments, the present invention comprises an LDV Fc molecule that is capable of binding to protein A and/or protein G, wherein said LDV Fc molecule comprises two lysine residues within the Fc domain and has a pyroglutamate residue at its N-terminus. In a particular example of this embodiment, the lysine residues are retained at positions 392 and 414 within the Fc domain. Alternatively, the lysine residues may be retained at two positions selected from: 222, 246, 248, 274, 288, 290, 317, 320, 322, 326, 334, 340, 360, 370, 392, 409, 414, 439 or 447. One or both of the lysine residues may also be located at a non-native position, such as residues: 358, 362, 364, 398, 416, 422 or 446.

The lysine residue located at position 447 located at the C-terminal position of the Fc domain is often removed using a carboxypeptidase. Accordingly, in the present invention, this lysine residue may be substituted by another amino acid residue, deleted by means such as enzymatic cleavage, or may be omitted from a nucleic acid molecule that encodes an Fc domain, such that the lysine at position 447 is not present.

In another aspect of the present invention, the LDV Fc domain is fused to an amino acid sequence encoding a targeting or active peptide. The targeting or active peptide may comprise any functional peptide, or fragment of the peptide that retains function, including, but not limited to, P-selectin glycoprotein ligand (PSGL-1). In certain embodiments, the amino acid sequence encoding the targeting or active peptide or peptide fragment does not contain any lysine residues. In other embodiments, the amino acid sequence encoding the targeting or active peptide or peptide fragment may have a single lysine residue. In such cases, the N-terminal amino acid of the targeting or active peptide may be replaced by glutamine (Q) or glutamic acid (E), and may be converted to pyroglutamate in order to eliminate the active amine. In particular embodiments of the invention, the targeting or active peptide comprises amino acids 1 through 47 of P-selectin glycoprotein ligand (PSGL-1). In other embodiments of the invention, the targeting or active peptide is selected from the group comprising erythropoietin an interleukin-3.

In certain embodiments, the present invention comprises fusion proteins comprising a targeting or active peptide that is fused or linked to an LDV Fc peptide (hereafter termed (Fusion-LDV Fc molecule"). The LDV Fc peptide of the Fusion-LDV Fc molecule may comprise an Fc domain wherein all lysine residues have been deleted by substitution with another amino acid residue. In such cases, the Fusion-LDV Fc molecule may have a unique reactive amine group at the N-terminus of the targeting or active peptide. In other embodiments, the Fusion-LDV Fc molecule is one that is capable of binding to protein A and/or protein G, wherein all lysine residues within the LDV Fc peptide have been replaced by other amino acids and wherein the targeting or active peptide comprises a pyroglutamate residue at its N-terminus. In these embodiments, the Fusion-LDV Fc molecule is devoid of all reactive amine groups.

In other embodiments, the present invention comprises a Fusion-LDV Fc molecule that is capable of binding to protein A and/or protein G, wherein said Fusion LDV Fc molecule comprises a single lysine residue retained within the Fc domain. The targeting or active peptide domain may have a reactive amine group, providing two potential reactive amine sites, or it may have a pyroglutamate residue at the N-terminus of the targeting or active peptide domain, in which case the retained lysine residue within the Fc domain provides the only reactive amine group in each chain. In particular examples of this embodiment, the single lysine residue is retained at position 392 or 414 within the Fc domain. Alternatively, the lysine residue may be retained at a position selected from: 222, 246, 248, 274, 288, 290, 317, 320, 322, 326, 334, 340, 360, 370, 392, 409, 414, 439 or 447. The single lysine residue may also be located at a non-native position, such as residues: 358, 362, 364, 398, 416, 422 or 446.

In other embodiments, the present invention comprises a Fusion-LDV Fc molecule that is capable of binding to protein A and/or protein G, wherein said Fusion-LDV Fc molecule comprises two lysine residues within the Fc domain. The targeting or active peptide domain may have a reactive amine group, providing a third potential reactive amine site in each chain, or may have a pyroglutamate residue at the N-terminus, in which case the retained lysine residue within the Fc domain provides the only reactive amine groups in each chain. In a particular example of this embodiment, the lysine residues are retained at positions 392 and 414 within the Fc domain. Alternatively, the lysine residues may be retained at two positions selected from: 222, 246, 248, 274, 288, 290, 317, 320, 322, 326, 334, 340, 360, 370, 392, 409, 414, 439 or 447. One or both of the lysine residues may also be located at a non-native position, such as residues: 358, 362, 364, 398, 416, 422 or 446.

BRIEF DESCRIPTION OF THE FIGURES

FIGS. 1A and 1B Schematic depiction of LDV-Fc molecules. (FIG. 1A) Each polypeptide chain of the LDV-Fc has all lysine residues replaced. The only reactive amine group is at the N-Terminus depicted by a star. (FIG. 1B) The N-Terminus of each polypeptide chain of the LDV-Fc has a pyroglutamate residue to remove the reactive amine. Each polypeptide chain of the LDV-Fc contains only a single lysine residue with its reactive amine group depicted with a star.

FIGS. 2A and 2B Schematic depiction of LDV-Fc Fusion molecules. (FIG. 2A) Each polypeptide chain of the LDV-Fc Fusion has all lysine residues replaced. The only reactive amine group is at the N-Terminus depicted by a star and fusion protein or peptide is at C-terminus of Fc via optional linker sequence. (FIG. 2B) The N-Terminus of each polypeptide chain of the LDV-Fc Fusion protein or peptide has a pyroglutamate residue to remove the reactive amine. Each polypeptide chain of the LDV-Fc Fusion contains only a single lysine residue with its reactive amine group depicted with a star and fusion is at N-terminus of Fc via optional linker sequence.

FIG. 3. An IgG Fc region amino acid sequence with Kabat numbering. Sequence is from human IgG1 Fc region. Lysine 248, reported to participate in protein G binding is in open circle. Lysine 338, reported to participate in protein A binding is in open rectangle.

FIG. 4. SD S-PAGE gel under reducing conditions and stained with Coomasie blue of a recombinant LDV-Fc molecule. The LDV-Fc was expressed and secreted from HEK293 cells. Conditioned medium was then subjected to protein A column purification.

FIG. 6B illustrates a human IgG-Fc-LDV, conjugated at the N-terminal amine group and having a C-terminal targeting sequence and conjugated at its N-terminal amine groups.). The fusion peptide is denoted as huIgG-Fc-LDV::ts.

FIG. 7 illustrates the intact mass difference between the main peaks of an IgG-Fc-LDV, devoid of all lysines before and after biotinylation reaction. The mass change of 679, indicates a homogeneous conjugation of two biotins (NHS-LC-Biotin) to the IgG-Fc-LDV molecule (non-reduced).

BRIEF DESCRIPTION OF THE SEQUENCES

Figure 5:
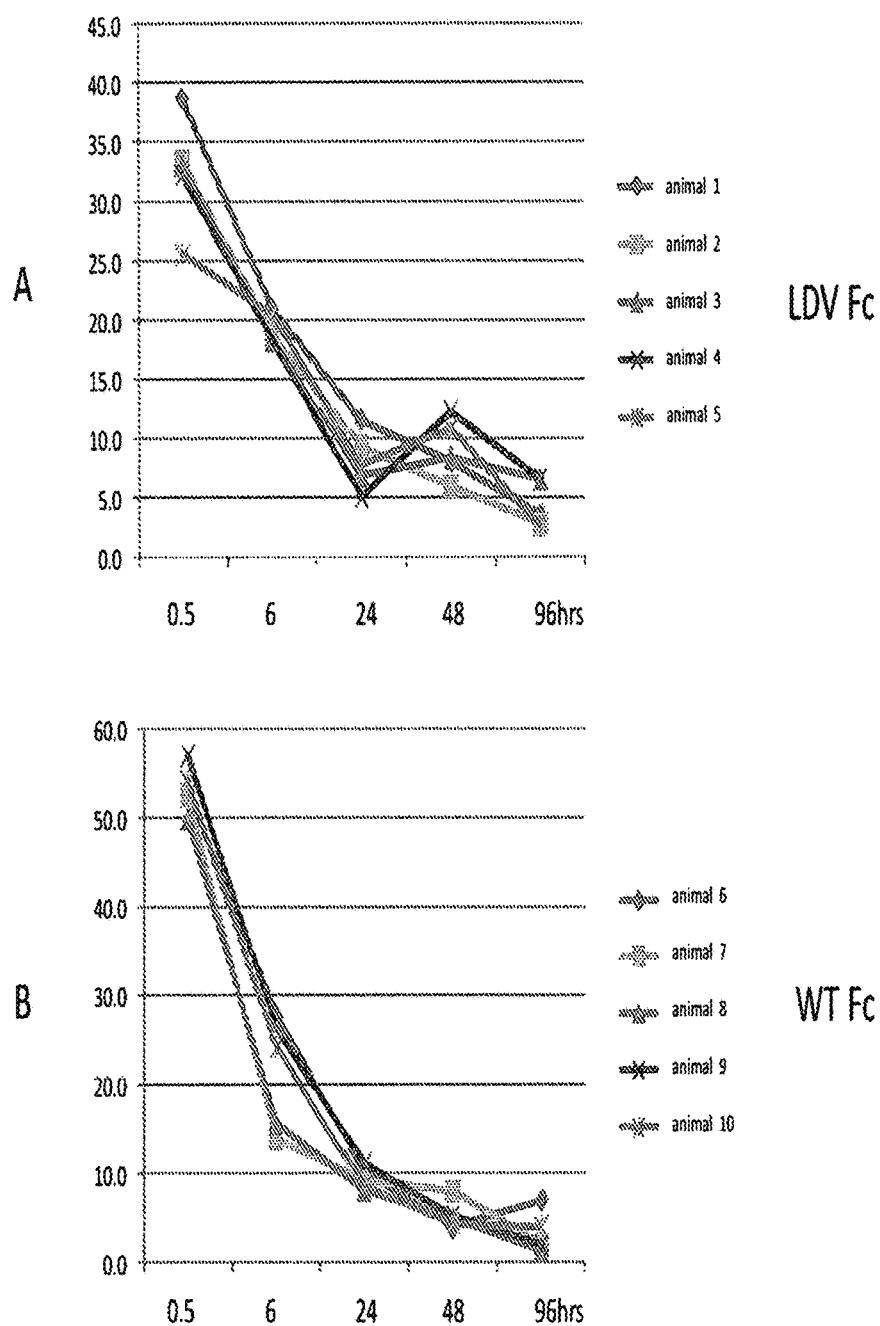
FIGS. 5A and 5B Comparison of pharmacokinetic profiles, over a 96 hours period, of a human IgG Fc devoid of lysine residues to a wild type human IgG Fc. Mice were injected intravenously in tail vein with either 5 mg/kg recombinant humanLDV-zeroK-IgG1 Fc (Group 1 FIG. 5A) or recombinant wild type human IgG1 Fc (Group 2 FIG. 5B). The X axis is time in hours. The Y axis values were determined by a serum ELISA assay.

Sequence ID No: 1 is the 227 amino acid sequence of the human immunoglobulin G1 Fc domain (IgG Fc), with 20 lysine residues.

Sequence ID No: 2 is the amino acid sequence of human PSGL-1.

Sequence ID No: 3 is the amino acid sequence of the principal binding site for P and L-selectin found within human PSGL-1.

Sequence ID No: 4 is a 47 amino acid sequence of PSGL-1 that includes the principal binding site and can be used to prepare soluble forms of PSGL-1 for use in preparing LDV-Fc fusion molecules of the present invention.

Sequence ID No: 5 is an amino acid sequence encoding a tandem soluble glycoprotein ligand (TSGL) comprising a 19 amino acid PSGL binding domain fused to an 11 amino acid PSGL (amino acids 9-19 of Sequence ID No: 3) binding domain, useful for preparing fusion molecules of the present invention.

Sequence ID No: 6: is the amino acid sequence of the cyclic peptide OS-1 useful for preparing fusion molecules of the present invention.

Sequence ID No: 7: is an amino acid sequence of a cyclic peptide useful for preparing fusion molecules of the present invention.

Sequence ID No: 8 is an amino acid sequence encoding LDV-Fc-0 fusion molecule of the present invention. The sequence comprises a signal peptide, followed by sequences encoding an N-terminal threonine Thr223 residue (Kabat) and an LDV-Fc region of human IgG1 devoid of all lysine residues.

Sequence ID No: 9 is an amino acid sequence encoding a TSGL-LDV-Fc fusion molecule of the present invention. The sequence comprises a signal peptide, tandem soluble PSGL-1 binding domains and an LDV-Fc region of human IgG1 at His224 (Kabat).

Sequence ID No: 10 is an amino acid sequence encoding an OS1-LDV-Fc fusion molecule of the present invention.

Sequence ID No: 11 is an amino acid sequence encoding a CCP-[PSGL1-19]-LDV-Fc fusion molecule of the present invention. The mature amino acid sequence of the encoded fusion protein begins with a glutamine (Q) which can be converted into an N-terminal pyroglutamate, at amino acid 20.

Sequence ID No: 12 is an amino acid sequence of a mature LDV Fc with a lysine residue at Kabat position 414 and an N-terminal targeting sequence. The LDV-Fc has added to it an 18 amino acid C-terminal tailpiece (-tp) from hIgM, and has the leucine residue at Kabat Position 309 altered to a cysteine to enable formation of inter-monomeric disulfide bridges, which allows the LDV-Fc fusion molecule to form polymeric LDV-Fc fusions, for example hexameric LDV-Fc fusions, as described in Mekhaiel et al. (2011), Scientific Reports, 1:124.

Sequence ID Nos. 13, 14 and 15 are amino acid sequences encoding flexible linkers of glycine and serine that are useful in the present invention.

Sequence ID Nos. 16 is a 226-amino acid fragment of a human IgG-Fc-region, mutated or engineered to eliminate all native lysine residues. This 226 amino acid fragment of human IgG-Fc is designated as IgG-Fc-LDV in Sequence ID No: 16.

Sequence ID Nos. 17 is a fusion protein comprising the 226 amino acid fragment IgG-Fc-LDV of Sequence No. 16, fused via a linker sequence (GGG in bold underline) to a 19 amino acid PSGL binding domain, [PSGL1-19], shown in green underlined text, to form a fusion protein of the present invention, designated as IgG-Fc-LDV-[PSGL1-19], in Sequence ID No. 17. In accordance with the present invention, the peptide shown in sequence ID No. 17 can be conjugated with another molecular entity, for example a polymer, or a microbubble.

Sequence ID Nos. 18 is a fusion protein comprising the 226 amino acid fragment IgG-Fc-LDV of Sequence No. 16 is fused via a linker sequence (GGG in bold underline) to a13 amino acid OS-1 cyclical peptide, shown in green underlined text, to form a fusion protein of the present invention, designated as IgG-Fc-LDV-[OS1], in Sequence ID No. 18. In accordance with the present invention, the peptide shown in sequence ID No. 18 can be conjugated with another molecular entity, for example a polymer, or a microbubble.

Sequence ID Nos. 19 is an alternative version of the LDV-Fc-0-protein that is devoid of all lysine residues, constructed by deleting the final lysine residue rather than by replacement with another residue, such as arginine. The amino acid sequence of this alternative LDV-Fc-0 protein is designated as Sequence ID No: 19. This 225 amino acid fragment IgG-Fc-LDV of Sequence No. 19 can be used as an alternative to the 226 amino acid fragment IgG-Fc-LDV of Sequence ID No. 16, and can be fused to a targeting sequence [such as a PSGL-1 binding sequence or an OS-1 sequence], and conjugated with a polymer or microbubble at the N-terminal residue.

DETAILED DESCRIPTION OF INVENTION AND ITS PREFERRED EMBODIMENTS

Components of the LDV-Fc Fusion Molecules

Human immunoglobulin G1 heavy chain is a 466 amino acid protein including a 227 amino acid fragment crystallizable (Fc) region (underlined) that interacts with cell surface receptors known as Fc receptors. The Fc region contains 20 lysine residues, and is designated Sequence ID No: 1. Fragments of the human IgG1 heavy chain useful in the present invention include those with starting points within five amino acids of the Asp 221 residue, for example, a fragment starting at residue Thr 223.

SEQ ID NO: 1:
DKTHTCPPCP APELLGGPSV FLFPPKPKDT LMISRTPEVT CVVVDVSHED PEVKFNWYVD

GVEVHNAKTK PREEQYNSTY RVVSVLTVLH QDWLNGKEYK CKVSNKALPA PIEKTISKAK

GQPREPQVYT LPPSRDELTK NQVSLTCLVK GFYPSDIAVE WESNGQPENN YKTTPPVLDS

DGSFFLYSKL TVDKSRWQQG NVFSCSVMHE ALHNHYTQKS LSLSPGK

Human PSGL-1 is 412 amino acid protein (designated Sequence ID No: 2) including a 17 amino acid N-terminal signal peptide (amino acids 1-17), a 24 amino acid N-terminal propeptide (amino acids 18-41) and a 371 amino acid P-selectin glycoprotein ligand 1 chain (amino acids 42-412).

Sequence ID No: 2:
MPLQLLLLLI LLGPGNSLQL WDTWADEAEK ALGPLLARDR RQATEYEYLD YDFLPETEPP

EMLRNSTDTT PLTGPGTPES TTVEPAARRS TGLDAGGAVT ELTTELANMG NLSTDSAAME

IQTTQPAATE AQTTQPVPTE AQTTPLAATE AQTTRLTATE AQTTPLAATE AQTTPPAATE

AQTTQPTGLE AQTTAPAAME AQTTAPAAME AQTTPPAAME AQTTQTTAME AQTTAPEATE

AQTTQPTATE AQTTPLAAME ALSTEPSATE ALSMEPTTKR GLFIPFSVSS VTHKGIPMAA

SNLSVNYPVG APDHISVKQC LLAILILALV ATIFFVCTVV LAVRLSRKGH MYPVRNYSPT

EMVCISSLLP DGGEGPSATA NGGLSKAKSP GLTPEPREDR EGDDLTLHSF LP

The principal binding site for P and L-selectin is found within a 19 amino acid segment at the amino terminus of the mature form of PSGL from amino acids 42 to 60 of Sequence ID No: 2 (Sequence ID No: 3).

Sequence ID No: 3:
QATEYEYLDY DFLPETEPP

Thus, soluble forms of PSGL-1 that include the principal binding site (amino acids 42 to 60 of Sequence ID No: 2, can be fused to a lysine depleted IgG Fc domain, and used in the present invention. One example of a suitable fragment of PSGL-1 includes amino acids 42 through 88 of Sequence ID No: 2, and is designated as Sequence ID NO: 4:

Sequence ID No: 4:
QATEYEYLDY DFLPETEPPE MLRNSTDTTP LTGPGTPEST TVEPAAR

Soluble tandem selectin glycoprotein ligands (TSGLs) are described in Shaw, US Patent Publication No. 2013/0136741, the disclosure of which is fully incorporated herein by reference. TSGLs comprise two or more sulfated glycoprotein peptide sequences from PSGL in a tandem configuration on a single polypeptide chain, providing for enhanced selectin binding activity. For example, a TSGL comprising a 19 amino acid PSGL (Sequence ID No: 3) binding domain fused to an 11 amino acid PSGL (9-19 of Sequence ID No: 3) binding domain is designated as Sequence ID No: 5:

Sequence ID No: 5:
QATEYEYLDY DFLPETEPPD YDFLPETEPP

Soluble forms of PSGL and TSGLs can be fused or linked to the LDV-Fc peptides of the present invention to form fusion PSGL-LDV-Fc molecules, or TSGL-LDV-Fc molecules, respectively of the present invention.

OS-1 is a synthetic amino acid cyclic peptide which is capable of binding to the N-terminal domain of GPlb-alpha, as described in Benard et al., Biochemistry, 47:4674-82 (2008). For example, the cyclic peptide OS-1, has the amino acid sequence designated as Sequence ID No: 6:

Sequence ID No: 6:
CTERMALHNL C

Shaw, US Patent Publication No. 2012/0165258, and PCT Patent Publication WO 2013/096932, extend the work of Benard et al., and describes derivatization of the OS-1 peptide to form other cyclic peptides (CPs). These OS-1-derived cyclic peptides may be used in the present invention, and my further be conjugated with polymers such as polyethylene glycol (PEG) to form conjugated cyclic peptides (CCPs). The CCPs are disclosed to demonstrate an enhanced activity for blocking specific interactions mediated by GPlb-alpha, compared to the unconjugated cyclic peptides. For example, one OS-1-derived cyclic peptide described in Shaw that may be used is described in Sequence ID No: 7

Sequence ID No: 7:
ACTERMALHN LCGG

OS-1, unconjugated versions of the OS-1-derived cyclic peptides disclosed in Shaw and CCPs disclosed in Shaw can be fused or linked to the LDV-Fc peptides of the present invention to form fusion OS-1-LDV-Fc molecules, CP-LDV-Fc molecules, or CCP-LDV-Fc molecules, respectively of the present invention.

Other peptides that can be utilized as the N-terminal peptides in the fusion molecules of the present invention include, but are not limited to, peptides targeted to cancer antigens, soluble receptors, cytokines, such as G-CSF, IL-3 and erythropoietin.

The free N-terminal amine group of an IgG-Fc fusion peptide can be eliminated in the following manner. The N-terminal amino acid may be replaced by glutamine (Q) or glutamic acid (E), and nearly completely converted to N-terminal pyroglutamate using methods in accordance with those described in Dick et al. (2007) Biotechnol. Bioeng., 97:544-553 and Lui et al. (2011), J. Biolog. Chem., 286: 11211-11217.

In certain embodiments of the present invention, one or two lysine residues may be introduced into the LDV-Fc peptide at a non-native position, using methods such as those described in Marquette et al., WO 2013/093809. Potential molecules for covalent chemical conjugation at amines of IgG LDV-Fc include but are not limited to small molecule drugs, radionuclides, chemotherapeutics, cytostatic agents, cytotoxic agents, biotin, polyethylene glycol, RNA, siRNA, fluorescent dyes, peptides and DNA aptamers. The full disclosure of WO 2013/093809 is hereby incorporated herein by reference.

Recombinant LDV-Fc molecules can be expressed and purified from transformed mammalian host cells such as a Chinese hamster ovary cells (CHO), HEK293 cells, or COS cells using recombinant DNA techniques and expression vectors as known in the art. Suitable engineered mammalian host cells are also capable of providing posttranslational modifications required to generate functional LDV-Fc molecules. Such capability may arise by virtue of the presence of a suitable glycosylating enzyme within the host cell, whether naturally occurring, induced by chemical mutagenesis, or through transfection of the host cell with a suitable expression plasmid containing a DNA sequence encoding the glycosylating enzyme. For example, host cells can be transfected with expression vectors to enable, via posttranslational modification, the generation of the sialyl Lewis' epitope on the N-linked and O-linked glycans of enhanced PSGL polypeptides. In the case of CHO cells, this requires the co-expression of an α-1,3/1,4 fucosyltranseferase (Kukowska-Latallo et al., Genes Dev. 4:1288-303, 1990) and Core2 β-1,6-N-acetylglucosaminyltransferase enzymes (Kumar et al., Blood 88:3872-79, 1996). The presence of the sialyl Lewis X epitopes on the N-linked and O-linked glycans of enhanced PSGL and/or immunoglobulin polypeptides may enhance the binding to selectins. In order to optimize processing of the mature N-terminus, these host cells may also be transfected with expression vectors with cDNA encoding a form of PACE, also known as furin, is disclosed in van den Ouweland et al., Nucl. Acids Res. 18, 664 (1990), the full disclosure of which is hereby incorporated herein by reference. Other host cells for production of LDV-Fc molecules include bacterial cells (U.S. Pat. No. 4,904,584 and Jung et al., PNAS 107: 604-609 (2010) insect cells, plant cells and yeast cells (Loos et al., Archives of Biochemistry and biophysics 526:167-173 (2012).)

The principal binding site contains three tyrosines residues [at amino acids 5, 7 and 10 of Sequence ID No: 2] for potential sulfation; and one threonine residue [at amino acid residue 16 of Sequence ID No: 2] for an O-linked glycan bearing a sialyl Lewis x (sLe$^x$) epitope. Accordingly, in a preferred embodiment, each monomeric sulfated PSGL-1 ligand binding domain contained within the TSGL proteins of the present invention may comprise at least amino acids residues 10 to 16 of Sequence ID No:2 (YDFLPET). In alternative embodiments, the monomeric sulfated PSGL-1 ligand binding domain may comprise one or more additional amino acids from the N-terminal end [e.g., amino acids 1-16; 2-16; 3-16; 4-16; 5-16; 6-16; 7-16; 8-16; or 9-16]; one or more additional amino acids from the C-terminal end [e.g., amino acids 10-17; 10-18; 10-19]; or one or more amino additional amino acids from both the N-terminal and C-terminal ends of Sequence ID No: 2: [e.g. amino acids: 1-17; 2-17; 3-17; 4-17; 5-17; 6-17; 7-17; 8-17; and 9-17; 1-18; 2-18; 3-18; 4-18; 5-18; 6-18; 7-18; 8-18; and 9-18; or 1-19; 2-19; 3-19; 4-19; 5-19; 6-19; 7-19; 8-19; and 9-19]. In certain embodiments, one or more tyrosine residues [of the three native tyrosine residues], may be altered for elimination of potential sulfation sites, provided that at least one tyrosine residue is present on the PSGL-1 ligand binding domain. In certain embodiments, the TSGL proteins of the present invention comprise at least two sulfated PSGL-1 ligand binding domains. In other embodiments, the TSGL proteins of the present invention may comprise at least one additional monomeric sulfated PSGL-1 ligand binding domain, that is, the TSGL protein comprises three or more sulfated PSGL-1 ligand binding domains TSGL proteins containing multiple sulfated residues increases the amount of negative (anionic) charge on the protein. TSGL proteins containing multiple sulfated residues can be purified from proteins having fewer sulfated residues (hyposulfated TSGL proteins) using methods similar to those described in U.S. Pat. No. 6,933,370. In certain embodiments, the TSGL proteins may be engineered such that one or more tyrosine residues [of the three native residues on each PSGL-1 ligand binding domain] is altered to eliminate potential sulfation sites, provided that at least one tyrosine residue is present on the TSGL protein. In certain embodiments, each PSGL-1 ligand binding domain present in a TSGL is altered to eliminate one or more potential sulfation sites, for example, by substitution of another amino acid for tyrosine, leaving an average of one sulfation site per PSGL-1 ligand binding domain. [For example, in a TSGL comprising two PSGL-1 ligand binding domains, the first PSGL-1 ligand binding domain may retain two tyrosines, while the second PSGL-1 ligand binding domain retains none]. In certain embodiments, the PSGL-1 ligand binding domain or each PSGL-1 ligand binding domain of the TSGL protein can be altered such that one or more potential sulfation sites is eliminated, and a tyrosine residue may be substituted for another amino acid residue to create one or more non-native potential sulfation sites.

In any fusion protein incorporating an LDV-Fc peptide, the amino acid sequence derived from one or more proteins other than the LDV-Fc can be linked to either the C-terminus or N-terminus of the LDV-Fc, or both. Fusion molecules of the present invention may be made by fusing the N-terminal amino acid sequences or C-terminal amino acid sequences derived from one or more other proteins (e.g., a fragment of a protein that exhibits a desired activity), to an LDV-Fc peptide of the present invention. The linkage may be direct (i.e., without an intervening linking sequence not derived from either protein) or through a linking sequence. In certain embodiments of the invention, the fusion LDV-Fc molecules are expressed from a recombinant DNA sequence which encodes both the LDV-Fc peptide and the N-terminal or C-terminal amino acid sequences, joined either directly or via a DNA sequence encoding a linker sequence.

In particular embodiments of the present invention, the Fc portion of immunoglobulin G (IgG-Fc) is modified to remove all of the amine groups such that the sole remaining amine reactive group is at the N-terminal residue of the IgG-Fc. The fully lysine-deleted variant is termed IgG-Fc-LDV. The lysine-depleted variants (LDV) of IgG Fc molecules still retain certain characteristic IgG Fc functions. They can stably form dimers, and can be purified using well-known techniques, such as purification using a Protein A and/or protein G columns.

Whether or not the IgG-Fc-LDV peptide is conjugated at the N-terminal residue, the IgG-Fc-LDV peptide can be joined or fused at the C-terminal residue with another sequence such as a targeting peptide sequence. In certain particular embodiments, the targeting peptide sequence joined or fused with IgG-Fc-LDV is selected from a P-selectin glycoprotein ligand-1 (PSGL-1) sequence, or a cyclical peptide, such as OS-1. Other targeting peptide sequences useful in the present invention include a number of intercellular adhesion molecules, such as mucosal addressing cellular adhesion molecule (MadCAM-1), [see Schippers et al. (2009), Gastroenterology 137:924-933], glycosylation dependent cell adhesion molecule (glyCAM-1) [see Rasmussen et al. (2002) Immunology Letters 83:73-75); podocalyxin [see Fernandez et al. (2013), Biochem. and Biophys. Research Communications 432:302-307]; and MUC-1 [See Oosterkamp et al. (1997) Int. J. Cancer 72:87-94].

Using procedures known in the art, the lysine-deleted variant of IgG-Fc (IgG-Fc-LDV) can be conjugated at the N-terminal residue with an amine-reactive molecule in an exclusive, site-specific manner. The IgG-Fc-LDV peptides of the present invention can be conjugated at the N-terminal residue with any molecule that contains an amine reactive group. For desired molecule that lack an amine reactive group, one can be engineered onto such molecule, using techniques known in the art. Suitable molecules for conjugation include polymers, such as polyethylene glycol (PEG) polymers, poly(lactic-co-glycolic acid) (PLGA) and its homopolymers, polyglycolic acid (PGA) and polylactic acid (PLA), as well as copolymers of the above. Other polymers useful in the present invention include carbohydrate biopolymers produced in nature, such as exopolysaccharides (EPS) and polyhydroxyalkanoates (PHAs). See Sukan et al. (2015) Carbohydrate Polymers, 126:47-51.

PEG, PLGA, PGA and PLA have all been established as safe in humans through long-term use in various biomedical systems, including as carriers for drug delivery. For example, U.S. Pat. No. 7,534,449 describes polymeric microparticles or nanoparticles, which can encapsulate or bind agents, such as therapeutic agents, nutritional agents, diagnostic and imaging agents, prophylactic agents, attachment molecules and mixtures thereof. See also, Kamaly et al., PNAS (2013), 110:6506-6511.

An IgG-Fc-LDV conjugated to a polymer can be incorporated into a microparticle, nanoparticle or microbubble. Microbubbles are generally gaseous spheres contained within a thin envelope or shell encompassing the gas. A microparticle, nanoparticle or microbubbles can be targeted using the IgG-Fc-LDV molecules of the present invention. In the case of microparticles or nanoparticles, the IgG-Fc-LDV can be used for targeting bioactive substances encased within or conjugated to the surface of the particle, such as therapeutic agents and diagnostic and imaging agents. In the case of microbubbles, the IgG-Fc-LDV can be used for targeting microbubbles to a vascular site for diagnostic imaging via ultrasound. Microbubbles may also be conjugated to the targeting agent via a biotin-avidin-biotin bridge. See Lindner et al., US Patent Application 2010/0196284. In certain embodiments, microbubbles may be conjugated at the N-terminus to the IgG-Fc-LDV molecules of the invention in order to form microbubble-conjugated-IgG-Fc-LDV (MB-IgG-Fc-LDV). The MB-IgG-Fc-LDV molecules may further be fused at its C-terminus to a targeting peptide sequence.

Figure 6:
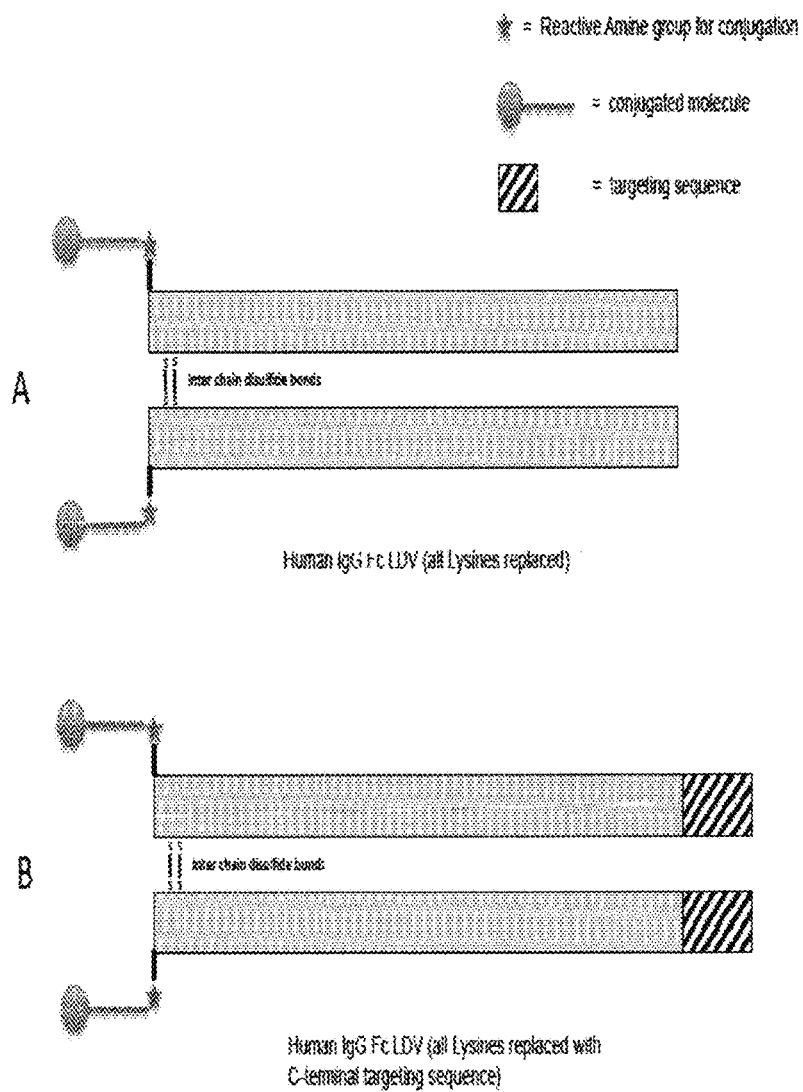
FIGS. 6A and 6B FIG. 6A illustrates a human IgG-Fc-LDV molecule conjugated at the N-terminal amine group.
Figure 7:
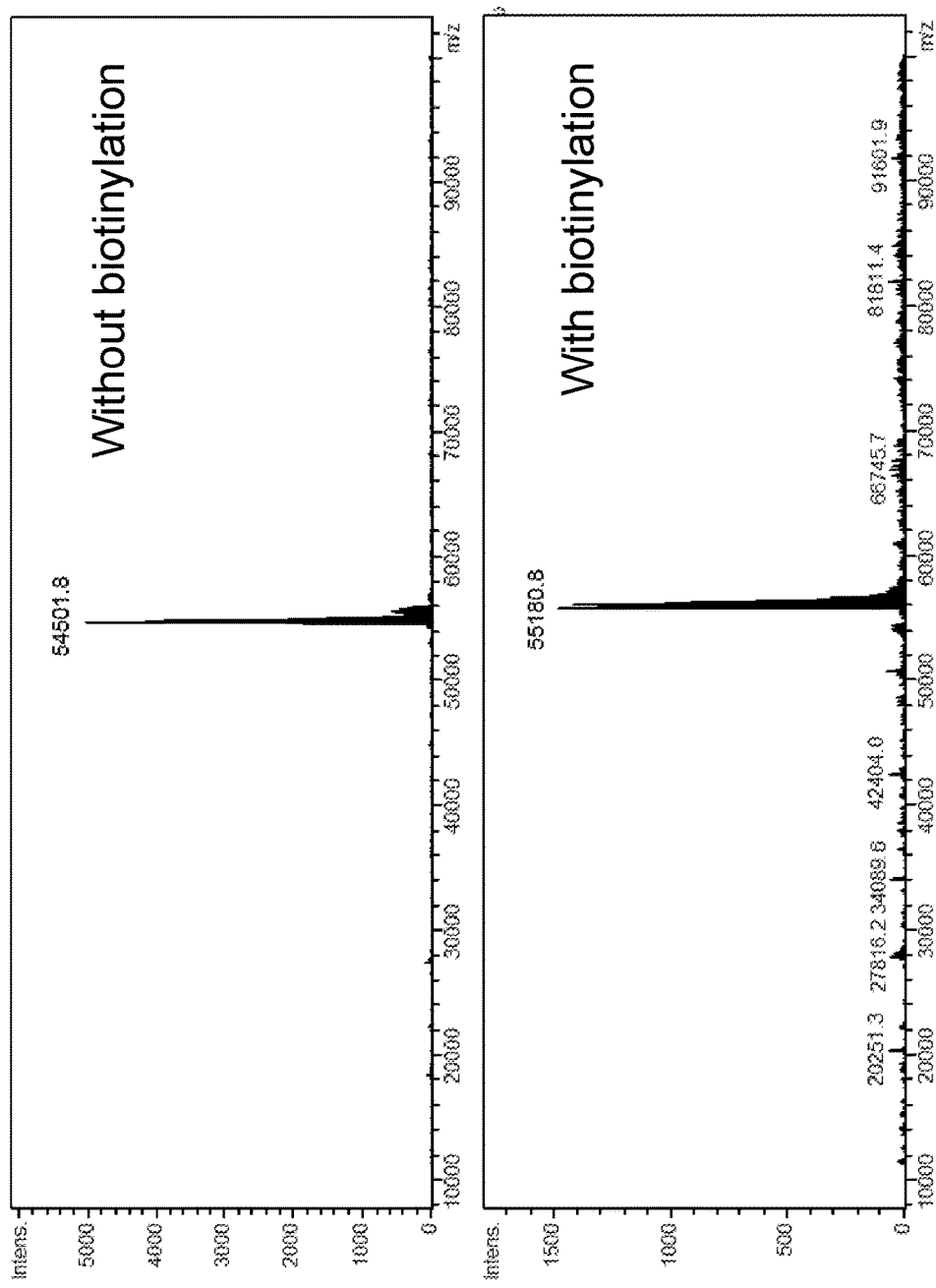
FIG. 7.

Because the IgG-Fc-LDV molecules have only a single reactive amine group present, the conjugation of the IgG-Fc-LDV molecule with amine-reactive polymeric molecules can be accomplished in a site-directed manner; that is, the amine-reactive polymeric molecule will only react at the N-terminal end of the IgG-Fc-LDV molecule. The IgG-Fc-LDV molecules can dimerize, forming dimeric IgG-Fc-LDV molecules which can be conjugated with amine-reactive polymeric molecules, in a site-directed manner such that the amine-reactive polymeric molecule will react at the N-terminal end of each chain, forming a dimeric molecule which is doubly conjugated; one polymeric molecule on each chain of the dimer. Accordingly, using the methods and materials of the present invention, IgG-Fc-LDV molecules of the present invention can be prepared in homogeneous compositions in which all of the available reactive amine sites are conjugated with the polymeric molecules. The conjugated dimeric IgG-Fc-LDV molecules of the present invention are illustrated in FIG. 6A. FIG. 6B illustrates the conjugated dimeric IgG-Fc-LDV molecules of the present invention in which the Ig-Fc-LDV domains have been fused to a C-terminal targeting sequence.

As used herein, the terms "conjugate" or "conjugated" when referring to molecules including peptides, means that two or more molecules are either directly coupled to each other or coupled through a chemical linker, including a biotin-avidin bridge. Generally, the IgG-Fc-LDV molecules of the present invention have only one, two, three or four sites available for amine reaction on each strand, such that the dimeric conjugated IgG-Fc-LDV molecules will be conjugated at two, four, six or eight sites, respectively, at a directed site or sites (i.e., sites with free amine groups, such as the N-terminal position (unless blocked, for example by conversion to pyroglutamate), and the lysine residues that remain, or have been engineered into the IgG-Fc-LDV molecule). As used herein, the terms “homogeneous” conjugate or “homogeneously” conjugated refers to molecules or compositions in which conjugation occurs at a directed site or sites, such that the homogeneous conjugated composition is predominantly comprised of molecules with conjugation occurring at the directed site or sites. In preferred embodiments of the invention, the homogeneously conjugated compositions of the present invention comprise molecules, wherein more than 70, 75, 80, 85, 90, 95, 97, 98 or 99% of the molecules are conjugated at the directed site or sites.

As used herein, the terms “fused” or “fusion” when referring to DNA molecules or peptides, means that two or more DNA molecules or peptides are either directly connected to each other, or connected through a linker sequence. Two or more DNA molecules can be connected, or ligated, to each other using known ligation techniques. Two or more peptides can be connected using known techniques for chemically joining amino acids. Alternatively, a fusion protein can be made recombinantly, using a DNA construct in which two or more DNA molecules have been fused together. The terms “fused” and “linked” can be used interchangeably to indicate that two or more DNA molecules or peptides are connected as described. Where two or more peptides are connected through a linker sequence, suitable peptide linker sequences are known in the art and include glycine-serine polymers (including, for example, (GS)n, (GSGGS)n (SEQ ID NO: 13), (GGGGS)n (SEQ ID NO: 14) and (GGGS)n (SEQ ID NO: 15), where n is an integer of at least one, e.g., one, two, three, or four), glycine-alanine polymers, alanine-serine polymers, and other flexible linkers. Other examples include peptide linkers described in U.S. Pat. No. 5,073,627, the disclosure of which is hereby incorporated by reference. For DNA molecules, suitable linker sequences would include nucleic acid sequences that encode the above peptide linker sequences.

Compositions and Formulations:

In certain embodiments, the composition further comprises one or more surfactants. Exemplary surfactants include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the surfactant is a Tween surfactant (e.g., Tween 60, Tween 80, etc.).

In certain embodiments, the composition further comprises one or more preservatives. Exemplary preservatives may include antioxidants, chelating agents, antimicrobial preservatives, antifungal preservatives, alcohol preservatives, acidic preservatives, and other preservatives.

In certain embodiments, the one or more preservative comprises an antioxidant. Exemplary antioxidants include, but are not limited to, phosphites, dibutyl phosphite, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, sodium sulfite, cysteine hydrochloride, thioglycerol, sodium mercaptoacetate, sodium formaldehyde sulfoxylate (SFS), lecithin, and alpha-tocopherol. In certain embodiments, the antioxidant is dibutyl phosphite or sodium bisulfite (NaHSO$_3$).

In certain embodiments, the one or more preservative comprises a chelating agent. Exemplary chelating agents include, but are not limited to, ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate.

In certain embodiments, the one or more preservative comprises an antimicrobial preservative. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

In certain embodiments, the one or more preservative comprises an antifungal preservative. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid.

In certain embodiments, the one or more preservative comprises an alcohol preservative. Exemplary alcohol preservatives include, but are not limited to, ethanol, polyethylene glycol, phenol, phenolic compounds, bisphenol, chlorobutanol, hydroxybenzoate, and phenylethyl alcohol.

In certain embodiments, the one or more preservative comprises an acidic preservative. Exemplary acidic preservatives include, but are not limited to, vitamin A, vitamin C, vitamin E, beta-carotene, citric acid, acetic acid, dehydroacetic acid, ascorbic acid, sorbic acid, and phytic acid.

Other preservatives include, but are not limited to, tocopherol, tocopherol acetate, deteroxime mesylate, cetrimide, butylated hydroxyanisol (BHA), butylated hydroxytouened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

In certain embodiments, the composition further comprises one or more diluents. Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

In certain embodiments, the composition further comprises one or more granulating and/or dispersing agents. Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

In certain embodiments, the composition further comprises one or more binding agents. Exemplary binding agents include, but are not limited to, starch (e.g. cornstarch and starch paste); gelatin; sugars (e.g. sucrose, glucose, dextrose, dextrin, molasses, lactose, lactitol, mannitol, etc.); natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; etc.; and combinations thereof.

In certain embodiments, the composition further comprises one or more buffering agents. Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

In certain embodiments, the composition further comprises one or more lubricating agents. Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

In certain embodiments, the composition further comprises one or more solubilizing or suspending agents. Exemplary solubilizing or suspending agents include, but are not limited to, water, organic solvents, oils, and mixtures thereof. Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof. In certain embodiments, the oil is mineral oil.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

The formulations of the pharmaceutical compositions described herein may be prepared by any method known or hereafter developed in the art of pharmacology. In general, such preparatory methods include the step of bringing the active ingredient (i.e., a glycosylated deltorphin variant) into association with a carrier and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) of the active ingredient.

Preferred dosage forms include oral and parenteral dosage forms. Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Compositions for oral administration are typically liquid or in solid dosage forms. Compositions for oral administration may include protease inhibitors, including organic acids such as citric acid, in order to inhibit pancreatic and brush border proteases. Compositions for oral administration may additionally include absorption enhancers, such as acylcarnitine and lauroylcarnitine, to facilitate the uptake of the peptide through the lumen of the intestine into the systemic circulation by a paracellular transport mechanism. Compositions for oral administration may additionally include detergents to improve the solubility of the peptides and excipients and to decrease interactions with intestinal mucus. Solid form compositions for oral administration, such as tablets or capsules, may typically comprise an enteric coating which further protects the peptides from stomach proteases and permits passage of the tablet or capsule into the small intestine. The solid form composition may additionally comprise a subcoat such as a non-ionic polymer. Examples of preparation of such orally available formulations are disclosed in U.S. Pat. No. 5,912,014, U.S. Pat. No. 6,086,918 and U.S. Pat. No. 6,673,574. The disclosure of each of these documents is hereby incorporated herein by reference.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, comprise 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* 21$^{st}$ ed., Lippincott Williams & Wilkins, 2005.

The skilled clinician will be able to determine the appropriate dosage amount and number of doses of an agent to be administered to subject, dependent upon both the age and weight of the subject, the underlying condition, and the response of an individual patient to the treatment. In addition, the clinician will be able to determine the appropriate timing for delivery of the agent in a manner effective to treat the subject.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Still further encompassed by the invention are kits that comprise one or more inventive complexes and/or compositions. Kits are typically provided in a suitable container (e.g., for example, a glass, foil, plastic, or cardboard package). In certain embodiments, an inventive kit may include one or more pharmaceutical excipients, pharmaceutical additives, therapeutically active agents, and the like, as described herein. In certain embodiments, an inventive kit may include means for proper administration, such as, for example, graduated cups, syringes, needles, cleaning aids, and the like. In certain embodiments, an inventive kit may include instructions for proper administration and/or preparation for proper administration.

Methods of Treatment:

The compositions and kits of the present invention are useful for the preparation of homogeneous conjugated compositions of IgG-Fc-LDV fusion proteins. IgG-Fc compositions are themselves used for intravenous immunoglobulin therapy (IVIG) to treat a wide range of autoimmune conditions. See Yu et al. (2013), J. Molecular Biology, 425:1253-58. Thus, for example, the conjugated IgG-Fc-LDV molecules will find use in methods of treatment of inflammation, inflammatory disorders and thrombosis. When fused to a targeting sequence, the IgG-Fc-LDV domains contribute to important characteristics such as stability, and provide a convenient means for purification, for example, using protein A chromatography or protein G chromatography. Such characteristics may improve the efficacy of the targeting domain; for example, IgG-Fc-LDV fusions with a PSGL-1 binding domain may be useful for treating conditions characterized by P-, E- or L-selectin mediated intercellular adhesion, which include many inflammatory and immunological conditions, as well as use in organ transplantation, treatment of ischemia and reperfusion, bacterial sepsis, and disseminated intravascular coagulation, adult respiratory distress syndrome and associated pulmonary disorders, tumor metastatsis, rheumatoid arthritis, thrombosis and atherosclerosis. They can also be used to reduce leukocyte adherence in ischemic myocardium, and hence enhance thrombolytic therapies. See, Shaw, U.S. Pat. No. 8,889,628.

Practice of the invention is illustrated in the following, non-limiting examples. The skilled artisan will recognize that many modifications, variations and extensions are possible while remaining within the teachings of the present specification and embodied within the claims.

Example 1

LDV-Fc-0 protein. A cDNA is constructed encoding a signal peptide, followed by sequences encoding an N-terminal threonine Thr223 residue (Kabat) and an LDV-Fc region of human IgG1 devoid of all lysine residues. The amino acid sequence of the LVD-Fc-0 protein is designated as Sequence ID No: 8.

Sequence ID No: 8

```
MEWSWVFLFF LSVTTGVHST HTCPPCPAPE ALGAPSVFLF PPRPRDTLMI SRTPEVTCVV

VDVSHEDPEV QFNWYVDGVE VHNAQTQPRE EQYNSTYRVV SVLTVLHQDW LNGREYRCRV

SNRALPAPIE RTISRARGQP REPQVYTLPP SRDELTQNQV SLTCLVRGFY PSDIAVEWES

NGQPENNYRT TPPVLDSDGS FFLYSRLTVD RSRWQQGNVF SCSVMHEALH NHYTQRSLSL

SPGR
```

It should be noted that the final lysine residue present in the IgG Fc domain is at the C-terminal end of the above region. Accordingly, an alternative version of the LDV-Fc-0-protein that is devoid of all lysine residues may be constructed by deleting the final lysine residue rather than by replacement with another residue, such as arginine. The amino acid sequence of this alternative LDV-Fc-0 protein is designated as Sequence ID No: 19.

Sequence ID No: 19

```
MEWSWVFLFF LSVTTGVHST HTCPPCPAPE ALGAPSVFLF PPRPRDTLMI SRTPEVTCVV

VDVSHEDPEV QFNWYVDGVE VHNAQTQPRE EQYNSTYRVV SVLTVLHQDW LNGREYRCRV

SNRALPAPIE RTISRARGQP REPQVYTLPP SRDELTQNQV SLTCLVRGFY PSDIAVEWES

NGQPENNYRT TPPVLDSDGS FFLYSRLTVD RSRWQQGNVF SCSVMHEALH NHYTQRSLSL

SPG
```

TSGL[PSGL1-19:PSGL6-19]-LDV-Fc.

A cDNA is constructed encoding the signal peptide, tandem soluble PSGL-1 binding domains and an LDV-Fc region of human IgG1 at His224 (Kabat). The amino acid sequence encoding TSGL-LDV-Fc fusion molecule is designated as Sequence ID No: 9. The mature amino acid sequence of the encoded fusion protein begins at amino acid 42 of Sequence ID No: 9. The mutations in the Fc portion include a change of Leu 234 and Gly237 of the native Fc sequence to Ala, and changes of Lys338 to Arg, and may optionally include changes of one or more Lys at 246, 248, 274, 288, 290, 317, 320, 322, 326, 334, 340, 360, 370, 392, 409, 414, 439 and 447 to amino acids other than Lys, especially Arg (R) and Glu (Q).

Sequence ID No: 9

```
MPLQLLLLLI LLGPGNSLQL WDTWADEAEK ALGPLLARDR RQATEYEYLD YDFLPETEPP

EYLDYDFLPE TEPPDKTHTC PPCPAPEALG APSVFLFPPK PKDTLMISRT PEVTCVVVDV

SHEDPEVKFN WYVDGVEVHN AKTKPREEQY NSTYRVVSVL TVLHQDWLNG KEYKCKVSNK

ALPAPIEKTI SKAKGQPREP QVYTLPPSRD ELTKNQVSLT CLVKGFYPSD IAVEWESNGQ

PENNYKTTPP VLDSDGSFFL YSKLTVDKSR WQQGNVFSCS VMHEALHNHY TQKSLSLSPG
K
```

Example 2

OS1-LDV-Fc Fusion Proteins.

A fusion molecule with a novel amino acid sequence can be constructed in accordance with the following procedure:

OS1-LDV-Fc:

A cDNA is constructed encoding the signal peptide, a PACE cleavage site and an eleven amino acid OS-1 sequence fused to a mutated LDV-Fc region of human IgG1 at His224 (Kabat et al.) of the native Fc sequence. O-linked glycans bearing the sialyl Lewis x (sLe$^x$) epitope occur at the Thr16 and Thr30 residues of the mature protein.

The amino acid sequence encoding OS1-LDV-Fc fusion molecule is designated as Sequence ID No: 10. The mutations in the Fc portion include a change of Leu 234 and Gly237 of the native Fc sequence to Ala, and changes of the following lysine residues: 246R, 248R, 274Q, 288Q, 290Q, 317R, 320R, 322R, 326R, 334R, 338R, 340R, 360Q, 370R, 392R, 409R, 439R and 447R. The lysine at residue 414 is maintained.

Sequence ID No: 10

```
CTERMALHNL CGGGDKTHTC PPCPAPEALG APSVFLFPPR PRDTLMISRT PEVTCVVVDV

SHEDPEVQFN WYVDGVEVHN AQTQPREEQY NSTYRVVSVL TVLHQDWLNG REYRCRVSNR

ALPAPIERTI SRARGQPREP QVYTLPPSRD ELTQNQVSLT CLVRGFYPSD IAVEWESNGQ

PENNYRTTPP VLDSDGSFFL YSRLTVDKSR WQQGNVFSCS VMHEALHNHY TQRSLSLSPG R
```

Example 3

CCP-[PSGL1-19]-LDV-Fc Fusion Proteins.

A fusion protein with a novel amino acid sequence can be constructed in accordance with the following procedure:

A cDNA is constructed encoding the 19 amino acid signal peptide, a PACE cleavage site, a 12 amino acid CCP and a 19 amino acid sulfated PSGL binding sequence fused to a mutated LDV-Fc region of human IgG1 at His224 (Kabat et al.) of the native Fc sequence. O-linked glycans bearing the sialyl Lewis x (sLe$^x$) epitope occur at the Thr16 and Thr30 residues of the mature protein.

The amino acid sequence encoding CCP-[PSGL1-19]-LDV-Fc fusion molecule is designated as Sequence ID No: 11. The mature amino acid sequence of the encoded fusion protein begins with a glutamine (Q) which can be converted into an N-terminal pyroglutamate, at amino acid 20 of Sequence ID No: 11. The mutations in the Fc portion include a change of Leu 234 and Gly237 of the native Fc sequence to Ala, and changes of the following lysine residues: 246R, 248R, 274Q, 288Q, 290Q, 317R, 320R, 322R, 326R, 334R, 338R, 340R, 360Q, 370R, 392R, 409R, 439R and 447R. The lysine at residue 414 is maintained.

Sequence ID No: 11

```
MEWSWVFLFF LSVTTGVHSQ ACTERMALHN LCGGGQATEY EYLDYDFLPE TEPPEGGGGA

GGGGDKTHTC PPCPAPEALG APSVFLFPPR PRDTLMISRT PEVTCVVVDV SHEDPEVQFN

WYVDGVEVHN AQTQPREEQY NSTYRVVSVL TVLHQDWLNG REYRCRVSNR ALPAPIERTI

SRARGQPREP QVYTLPPSRD ELTQNQVSLT CLVRGFYPSD IAVEWESNGQ PENNYRTTPP

VLDSDGSFFL YSRLTVDKSR WQQGNVFSCS VMHEALHNHY TQRSLSLSPG R
```

[PSGL1-19]-LDV-Fc-[huIgM C Terminal Tailpiece] Fusion Proteins.

A mature fusion protein with a novel amino acid sequence can be constructed in accordance with the following procedure:

A cDNA is constructed encoding the 19 amino acid sulfated PSGL binding sequence fused to a mutated LDV-Fc region of human IgG1 at His224 (Kabat et al.) of the native Fc sequence. For example, the 19 amino acid PSGL binding domain can be fused to a 227 amino acid IgG1 fragment engineered to eliminate all native lysine residues with the exception of a single lysine residue at Kabat position 414 (bold and underlined). The [PSGL1-19]-LDV-Fc fusion variant is fused to an 18 amino acid C-terminal tailpiece (-tp) from hIgM, and has the leucine residue at Kabat Position 309 altered to a cysteine to enable formation of inter-monomeric disulfide bridges, which allows the LDV-Fc fusion molecule to form polymeric LDV-Fc fusions, for example hexameric LDV-Fc fusions, as described in Mekhaiel et al. (2011), Scientific Reports, 1:124. The LDV-Fc fusion L309C variant, fused to the 18 amino acid C-terminal tailpiece from IgM to form the PSGL-LDV-Fc molecule below, designated as Sequence ID No. 12:

Sequence ID No: 12

Sequence ID No: 12

```
QATEYEYLDY DFLPETEPPE RTHTCPPCPA PEALGAPSVF LFPPRPRDTL MISRTPEVTC

VVVDVSHEDP EVQFNWYVDG VEVHNAQTQP REEQYNSTYR VVSVLTVCLQ DWLNGDEYRC

RVSNRALPAP IERTISRARG QPREPQVITL PPSRDELTQN QVSLTCLVRG FYPSDIAVEW

ESNGQPENNY RTTPPVLDSD GSFFLYSRLT VDKSRWQQGN VFSCSVMHEA LHNHYTQRSL

SLSPGRPTLY NVSLVMSDTA GTCY
```

Example 4

Conjugated-IgG-Fc-LDV-PSGL-1 Fusion Proteins.

A mature conjugated fusion protein with a novel amino acid sequence can be constructed in accordance with the following procedure:

A cDNA is constructed encoding a 226-amino acid fragment of a human IgG-Fc-region, mutated or engineered to eliminate all native lysine residues. This 226 amino acid fragment of human IgG-Fc is shown below, designated as IgG-Fc-LDV in Sequence ID No: 16.

```
Sequence ID No: 16
DRTHTCPPCP APEALGAPSV FLFPPRPRDT LMISRTPEVT CVVVDVSHED PEVQFNWYVD

GVEVHNAQTQ PREEQYNSTY RVVSVLTVLH QDWLNGREYR CRVSNRALPA PIERTISRAR

GQPREPQVYT LPPSRDELTQ NQVSLTCLVR GFYPSDIAVE WESNGQPENN YRTTPPVLDS

DGSFFLYSRL TVDRSRWQQG NVFSCSVMHE ALHNHYTQRS LSLSPG
```

The 226 amino acid fragment IgG-Fc-LDV of Sequence No. 16 is fused via a linker sequence (GGG in bold underline) to a19 amino acid PSGL binding domain, [PSGL1-19], shown in green underlined text, to form a fusion protein of the present invention, designated as IgG-Fc-LDV-[PSGL1-19], in Sequence ID No. 17. In accordance with the present invention, the peptide shown in sequence ID No. 17 can be conjugated with another molecular entity, for example a polymer, or a microbubble.

```
Sequence ID No: 17:
DRTHTCPPCP APEALGAPSV FLFPPRPRDT LMISRTPEVT CVVVDVSHED PEVQFNWYVD

GVEVHNAQTQ PREEQYNSTY RVVSVLTVLH QDWLNGREYR CRVSNRALPA PIERTISPAR

GQPREPQVYT LPPSRDELTQ NQVSLTCLVR GFYPSDIAVE WESNGQPENN YRTTPPVLDS

DGSFELYSRL TVDRSRWQQG NVFSCSVMHE ALHNHYTQRS LSLSPGGGGQ ATEYEYLDYD

FLPETEPP
```

Alternatively, the 226 amino acid fragment IgG-Fc-LDV of Sequence No. 16 is fused via a linker sequence (GGG in bold underline) to a13 amino acid OS-1 cyclical peptide, shown in green underlined, to form a fusion protein of the present invention, designated as IgG-Fc-LDV-[OS1], in Sequence ID No. 18. In accordance with the present invention, the peptide shown in sequence ID No. 18 can be conjugated with another molecular entity, for example a polymer, or a microbubble.

```
Sequence ID No: 18:
DRTHTCPPCP APEALGAPSV FLFPPRPRDT LMISRTPEVT CVVVDVSHED PEVQFNWYVD

GVEVHNAQTQ PREEQYNSTY RVVSVLTVLH QDWLNGREYR CRVSNRALPA PIERTISPAR

GQPREPQVYT LPPSRDELTQ NQVSLTCLVR GFYPSDIAVE WESNGQPENN YRTTPPVLDS

DGSFELYSRL TVDRSRWQQG NVFSCSVMHE ALHNHYTQRS LSLSPGGGGC TERMALHNLC
```

Example 5: Conjugation of IgG-Fc-LDV Molecules Using Biotin Reaction

EZ-Link® NHS-biotin (Thermo Scientific) is equilibrated to room temperature. Approximately 1-10 mg protein is dissolved in 0.5-2.0 mL PBS according to the manufacturer's instructions Immediately before use, 10 mM solution of the biotin reagent is prepared in an organic solvent such as dimethylsulfoxide (DMSO) or dimethylformamide (DMF). For NHS-Biotin N-hydroxysuccinimidobiotin (Product No. 20217), 2.0 mg reagent is dissolved in 590 µL of solvent. Add the appropriate volume of 10 mM biotin reagent solution to the protein solution and incubate reaction on ice for two hours or at room temperature for 30 minutes.

Example 6: Purification and Testing of Fusion Proteins of LDV-Fc Molecules

Because the LDV-Fc domains retain the ability to bind to Protein A and Protein G, the fusion proteins can be purified using standard Protein A and Protein G purification schemes provided by the manufacturers. For example, see "Purification of IgG Using Protein A- or Protein-G Agarose" (KPL), downloaded from http://www.kpl.com/docs/techdocs/PURI-FIGG.PDF. See also, Page and Thorpe, "Purification of IgG Using Protein A or Protein G" from The Protein Protocols Handbook, (J. Walker, Ed.) (Humana Press, 2002).

Example 7: Activity of OS1/CCP/PSGL/TSGL Fusions

To confirm activity of CCP-[PSGL1-19]-LDV-Fc molecules, purified CCP-[PSGL1-19]-LDV-Fc molecules are immobilized on an Octet biosensor (Pall Fortebio Corp, Menlo Park, Calif.) and mixed with recombinant human CD42b/GPIb (R&D Systems Cat 4067-GP). Octet assay is then performed. For platelet function assays see Benard et al., Biochemistry, 47:4674-82 (2008).

Fusion proteins of the present invention comprising OS1, OS1-derived cyclic peptides (CP) and conjugated cyclic peptides (CPP), and one or more soluble PSGL-1 ligand binding domains (e.g., tandem soluble PSGL-1 ligand binding domains, or TSGL) can be tested in similar fashion. Additional testing of activity of the fusion proteins can be conducted in accordance with the methods disclosed in Shaw et al., WO 2011/162831, WO 2013/096932 and WO2013/082200.

Example 8: Pharmacokinetics of Fusion Proteins LDV-Fc Molecules

Mice were injected intravenously in tail vein with either 5 mg/kg recombinant humanLDV-zeroK-IgG1 Fc (Group 1) or recombinant wild type human IgG1 Fc (Group 2), and pharmacokinetic profiles were compared over a 96 hours period, and are illustrated in FIG. 5. The X axis is time in hours. The Y axis is measurement of protein concentration over time; Y axis values were determined by a serum ELISA assay. This experiment demonstrates that the pharmacokinetic properties of the lysine-depleted IgG1 variants of the present invention (A) remained essentially unchanged from those of wild-type IgG1 (B). This is surprising and unexpected in light of the teaching in the scientific literature that at least one lysine at residue 338, is critical for binding of IgG1 to Protein A.

All patents, patent applications and scientific literature references that are cited in the disclosure are hereby incorporated herein for the cited teachings, as if fully set forth.

What is claimed is:

1. A molecule comprising a conjugated, lysine-depleted variant of an immunoglobulin G Fc (IgG-Fc-LDV) domain, comprising an amino acid sequence of IgG-Fc wherein all of the native lysine residues have been replaced with a different amino acid residue selected from the group of amino acids that excludes cysteine, methionine, proline and lysine, and wherein said IgG-Fc-LDV is conjugated in a site specific manner at its N-terminus with a polymeric molecule.

2. The molecule of claim 1, wherein said IgG-Fc-LDV comprises the amino acid sequence of SEQ ID NO: 16.

3. A targeted fusion peptide molecule comprising the molecule of claim 1, further comprising a targeting peptide sequence, wherein the targeting peptide sequence is fused to the C-terminal peptide of IgG-Fc-LDV.

4. The targeted fusion peptide molecule of claim 3, wherein said targeting peptide sequence is a PSGL-1 binding sequence.

5. The targeted fusion peptide molecule of claim 4, wherein said targeted IgG-Fc-LDV fusion peptide molecule comprises the amino acid sequence of SEQ ID NO: 17.

6. The targeted fusion peptide molecule of claim 3, wherein said targeting peptide sequence is an OS-1 peptide sequence.

7. The targeted fusion peptide molecule of claim 6, wherein said targeted IgG-Fc-LDV fusion peptide molecule comprises the amino acid sequence of SEQ ID NO: 18.

8. The molecule of claim 1, wherein the IgG-Fc-LDV domain is conjugated at its N-terminus to a microbubble or nanoparticle.

9. The targeted fusion peptide molecule of claim 3, wherein the targeted IgG-Fc-LDV domain is conjugated to a microbubble or nanoparticle.

10. The targeted fusion peptide molecule of claim 5, wherein the IgG-Fc-LDV domain is conjugated to a microbubble or nanoparticle.

11. The targeted fusion peptide molecule of claim 7, wherein the IgG-Fc-LDV domain is conjugated to a microbubble or nanoparticle.

12. A method of producing homogeneous conjugated immunoglobulin G Fc domains, comprising replacing all native lysine residue in the IgG Fc domain with a different amino acid residue selected from the group of amino acids that excludes cysteine, methionine, proline and lysine, in order to form a lysine-deleted variant (IgG-Fc-LDV) domain, and thereafter conjugating said IgG-Fc-LDV domain with a polymeric molecule.

13. The method of claim 12, wherein the IgG-Fc-LDV domain is produced recombinantly from a nucleic acid molecule encoding an IgG-Fc domain, in which substitutions have been made to replace all DNA sequences encoding native lysine residue in the IgG Fc domain with DNA sequences encoding a different amino acid residue selected from the group of amino acids that excludes cysteine, methionine, proline and lysine.

14. The method of claim 12, wherein IgG-Fc-LDV domain comprises the amino acid sequence of SEQ ID NO: 16.

15. The method of claim 13, wherein IgG-Fc-LDV domain comprises the amino acid sequence of SEQ ID NO: 16.

16. The method of claim 12, wherein the polymeric molecule is a microbubble or nanoparticle.

* * * * *

SEQUENCE LISTING

```
<160> NUMBER OF SEQ ID NOS: 19

<210> SEQ ID NO 1
<211> LENGTH: 227
<212> TYPE: PRT
<213> ORGANISM: homo sapiens

<400> SEQUENCE: 1

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 2
<211> LENGTH: 412
<212> TYPE: PRT
<213> ORGANISM: Homo sapiens
```

<400> SEQUENCE: 2

```
Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Gln Ala Thr Glu Tyr Glu Tyr
            35                  40                  45

Leu Asp Tyr Asp Phe Leu Pro Glu Thr Glu Pro Glu Met Leu Arg
    50                  55                  60

Asn Ser Thr Asp Thr Thr Pro Leu Thr Gly Pro Gly Thr Pro Glu Ser
65                  70                  75                  80

Thr Thr Val Glu Pro Ala Ala Arg Arg Ser Thr Gly Leu Asp Ala Gly
                85                  90                  95

Gly Ala Val Thr Glu Leu Thr Thr Glu Leu Ala Asn Met Gly Asn Leu
                100                 105                 110

Ser Thr Asp Ser Ala Ala Met Glu Ile Gln Thr Thr Gln Pro Ala Ala
            115                 120                 125

Thr Glu Ala Gln Thr Thr Gln Pro Val Pro Thr Glu Ala Gln Thr Thr
130                 135                 140

Pro Leu Ala Ala Thr Glu Ala Gln Thr Thr Arg Leu Thr Ala Thr Glu
145                 150                 155                 160

Ala Gln Thr Thr Pro Leu Ala Ala Thr Glu Ala Gln Thr Thr Pro Pro
                165                 170                 175

Ala Ala Thr Glu Ala Gln Thr Thr Gln Pro Thr Gly Leu Glu Ala Gln
                180                 185                 190

Thr Thr Ala Pro Ala Ala Met Glu Ala Gln Thr Thr Ala Pro Ala Ala
            195                 200                 205

Met Glu Ala Gln Thr Thr Pro Pro Ala Ala Met Glu Ala Gln Thr Thr
210                 215                 220

Gln Thr Thr Ala Met Glu Ala Gln Thr Thr Ala Pro Glu Ala Thr Glu
225                 230                 235                 240

Ala Gln Thr Thr Gln Pro Thr Ala Thr Glu Ala Gln Thr Thr Pro Leu
                245                 250                 255

Ala Ala Met Glu Ala Leu Ser Thr Glu Pro Ser Ala Thr Glu Ala Leu
                260                 265                 270

Ser Met Glu Pro Thr Thr Lys Arg Gly Leu Phe Ile Pro Phe Ser Val
            275                 280                 285

Ser Ser Val Thr His Lys Gly Ile Pro Met Ala Ala Ser Asn Leu Ser
290                 295                 300

Val Asn Tyr Pro Val Gly Ala Pro Asp His Ile Ser Val Lys Gln Cys
305                 310                 315                 320

Leu Leu Ala Ile Leu Ile Leu Ala Leu Val Ala Thr Ile Phe Phe Val
                325                 330                 335

Cys Thr Val Val Leu Ala Val Arg Leu Ser Arg Lys Gly His Met Tyr
            340                 345                 350

Pro Val Arg Asn Tyr Ser Pro Thr Glu Met Val Cys Ile Ser Ser Leu
            355                 360                 365

Leu Pro Asp Gly Gly Glu Gly Pro Ser Ala Thr Ala Asn Gly Gly Leu
    370                 375                 380

Ser Lys Ala Lys Ser Pro Gly Leu Thr Pro Glu Pro Arg Glu Asp Arg
385                 390                 395                 400

Glu Gly Asp Asp Leu Thr Leu His Ser Phe Leu Pro
                405                 410
```

```
<210> SEQ ID NO 3
<211> LENGTH: 19
<212> TYPE: PRT
<213> ORGANISM: Homo sapiens

<400> SEQUENCE: 3

Gln Ala Thr Glu Tyr Glu Tyr Leu Asp Tyr Asp Phe Leu Pro Glu Thr
1               5                   10                  15

Glu Pro Pro

<210> SEQ ID NO 4
<211> LENGTH: 47
<212> TYPE: PRT
<213> ORGANISM: homo sapiens

<400> SEQUENCE: 4

Gln Ala Thr Glu Tyr Glu Tyr Leu Asp Tyr Asp Phe Leu Pro Glu Thr
1               5                   10                  15

Glu Pro Pro Glu Met Leu Arg Asn Ser Thr Asp Thr Thr Pro Leu Thr
            20                  25                  30

Gly Pro Gly Thr Pro Glu Ser Thr Thr Val Glu Pro Ala Ala Arg
        35                  40                  45

<210> SEQ ID NO 5
<211> LENGTH: 30
<212> TYPE: PRT
<213> ORGANISM: Artificial Sequence
<220> FEATURE:
<223> OTHER INFORMATION: Synthesized

<400> SEQUENCE: 5

Gln Ala Thr Glu Tyr Glu Tyr Leu Asp Tyr Asp Phe Leu Pro Glu Thr
1               5                   10                  15

Glu Pro Pro Asp Tyr Asp Phe Leu Pro Glu Thr Glu Pro Pro
            20                  25                  30

<210> SEQ ID NO 6
<211> LENGTH: 11
<212> TYPE: PRT
<213> ORGANISM: Artificial Sequence
<220> FEATURE:
<223> OTHER INFORMATION: Synthesized

<400> SEQUENCE: 6

Cys Thr Glu Arg Met Ala Leu His Asn Leu Cys
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthesized

<400> SEQUENCE: 7

Ala Cys Thr Glu Arg Met Ala Leu His Asn Leu Cys Gly Gly
1               5                   10

<210> SEQ ID NO 8
<211> LENGTH: 244
<212> TYPE: PRT
<213> ORGANISM: Artificial Sequence
<220> FEATURE:
<223> OTHER INFORMATION: Synthesized
```

<400> SEQUENCE: 8

```
Met Glu Trp Ser Trp Val Phe Leu Phe Phe Leu Ser Val Thr Thr Gly
1               5                   10                  15

Val His Ser Thr His Thr Cys Pro Pro Cys Pro Ala Pro Glu Ala Leu
            20                  25                  30

Gly Ala Pro Ser Val Phe Leu Phe Pro Pro Arg Pro Arg Asp Thr Leu
        35                  40                  45

Met Ile Ser Arg Thr Pro Glu Val Thr Cys Val Val Asp Val Ser
    50                  55                  60

His Glu Asp Pro Glu Val Gln Phe Asn Trp Tyr Val Asp Gly Val Glu
65                  70                  75                  80

Val His Asn Ala Gln Thr Gln Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Arg Glu Tyr Arg Cys Arg Val Ser Asn Arg Ala Leu Pro Ala Pro
        115                 120                 125

Ile Glu Arg Thr Ile Ser Arg Ala Arg Gly Gln Pro Arg Glu Pro Gln
    130                 135                 140

Val Tyr Thr Leu Pro Pro Ser Arg Asp Glu Leu Thr Gln Asn Gln Val
145                 150                 155                 160

Ser Leu Thr Cys Leu Val Arg Gly Phe Tyr Pro Ser Asp Ile Ala Val
                165                 170                 175

Glu Trp Glu Ser Asn Gly Gln Pro Glu Asn Asn Tyr Arg Thr Thr Pro
            180                 185                 190

Pro Val Leu Asp Ser Asp Gly Ser Phe Phe Leu Tyr Ser Arg Leu Thr
        195                 200                 205

Val Asp Arg Ser Arg Trp Gln Gln Gly Asn Val Phe Ser Cys Ser Val
    210                 215                 220

Met His Glu Ala Leu His Asn His Tyr Thr Gln Arg Ser Leu Ser Leu
225                 230                 235                 240

Ser Pro Gly Arg
```

<210> SEQ ID NO 9
<211> LENGTH: 301
<212> TYPE: PRT
<213> ORGANISM: Artificial Sequence
<220> FEATURE:
<223> OTHER INFORMATION: Synthesized

<400> SEQUENCE: 9

```
Met Pro Leu Gln Leu Leu Leu Leu Ile Leu Leu Gly Pro Gly Asn
1               5                   10                  15

Ser Leu Gln Leu Trp Asp Thr Trp Ala Asp Glu Ala Glu Lys Ala Leu
            20                  25                  30

Gly Pro Leu Leu Ala Arg Asp Arg Arg Gln Ala Thr Glu Tyr Glu Tyr
        35                  40                  45

Leu Asp Tyr Asp Phe Leu Pro Glu Thr Glu Pro Pro Glu Tyr Leu Asp
    50                  55                  60

Tyr Asp Phe Leu Pro Glu Thr Glu Pro Asp Lys Thr His Thr Cys
65                  70                  75                  80

Pro Pro Cys Pro Ala Pro Glu Ala Leu Gly Ala Pro Ser Val Phe Leu
                85                  90                  95

Phe Pro Pro Lys Pro Lys Asp Thr Leu Met Ile Ser Arg Thr Pro Glu
            100                 105                 110
```

```
Val Thr Cys Val Val Asp Val Ser His Glu Asp Pro Glu Val Lys
        115                 120                 125

Phe Asn Trp Tyr Val Asp Gly Val Glu Val His Asn Ala Lys Thr Lys
130                 135                 140

Pro Arg Glu Glu Gln Tyr Asn Ser Thr Tyr Arg Val Val Ser Val Leu
145                 150                 155                 160

Thr Val Leu His Gln Asp Trp Leu Asn Gly Lys Glu Tyr Lys Cys Lys
                165                 170                 175

Val Ser Asn Lys Ala Leu Pro Ala Pro Ile Glu Lys Thr Ile Ser Lys
            180                 185                 190

Ala Lys Gly Gln Pro Arg Glu Pro Gln Val Tyr Thr Leu Pro Pro Ser
        195                 200                 205

Arg Asp Glu Leu Thr Lys Asn Gln Val Ser Leu Thr Cys Leu Val Lys
    210                 215                 220

Gly Phe Tyr Pro Ser Asp Ile Ala Val Glu Trp Glu Ser Asn Gly Gln
225                 230                 235                 240

Pro Glu Asn Asn Tyr Lys Thr Thr Pro Pro Val Leu Asp Ser Asp Gly
                245                 250                 255

Ser Phe Phe Leu Tyr Ser Lys Leu Thr Val Asp Lys Ser Arg Trp Gln
            260                 265                 270

Gln Gly Asn Val Phe Ser Cys Ser Val Met His Glu Ala Leu His Asn
        275                 280                 285

His Tyr Thr Gln Lys Ser Leu Ser Leu Ser Pro Gly Lys
    290                 295                 300

<210> SEQ ID NO 10
<211> LENGTH: 241
<212> TYPE: PRT
<213> ORGANISM: Artificial Sequence
<220> FEATURE:
<223> OTHER INFORMATION: Synthesized

<400> SEQUENCE: 10

Cys Thr Glu Arg Met Ala Leu His Asn Leu Cys Gly Gly Gly Asp Lys
1               5                   10                  15

Thr His Thr Cys Pro Pro Cys Pro Ala Pro Glu Ala Leu Gly Ala Pro
            20                  25                  30

Ser Val Phe Leu Phe Pro Pro Arg Pro Arg Asp Thr Leu Met Ile Ser
        35                  40                  45

Arg Thr Pro Glu Val Thr Cys Val Val Val Asp Val Ser His Glu Asp
    50                  55                  60

Pro Glu Val Gln Phe Asn Trp Tyr Val Asp Gly Val Glu Val His Asn
65                  70                  75                  80

Ala Gln Thr Gln Pro Arg Glu Glu Gln Tyr Asn Ser Thr Tyr Arg Val
                85                  90                  95

Val Ser Val Leu Thr Val Leu His Gln Asp Trp Leu Asn Gly Arg Glu
            100                 105                 110

Tyr Arg Cys Arg Val Ser Asn Arg Ala Leu Pro Ala Pro Ile Glu Arg
        115                 120                 125

Thr Ile Ser Arg Ala Arg Gly Gln Pro Arg Glu Pro Gln Val Tyr Thr
    130                 135                 140

Leu Pro Pro Ser Arg Asp Glu Leu Thr Gln Asn Gln Val Ser Leu Thr
145                 150                 155                 160

Cys Leu Val Arg Gly Phe Tyr Pro Ser Asp Ile Ala Val Glu Trp Glu
                165                 170                 175
```

```
Ser Asn Gly Gln Pro Glu Asn Asn Tyr Arg Thr Thr Pro Pro Val Leu
            180                 185                 190

Asp Ser Asp Gly Ser Phe Phe Leu Tyr Ser Arg Leu Thr Val Asp Lys
            195                 200                 205

Ser Arg Trp Gln Gln Gly Asn Val Phe Ser Cys Ser Val Met His Glu
    210                 215                 220

Ala Leu His Asn His Tyr Thr Gln Arg Ser Leu Ser Leu Ser Pro Gly
225                 230                 235                 240

Arg

<210> SEQ ID NO 11
<211> LENGTH: 291
<212> TYPE: PRT
<213> ORGANISM: Artificial Sequence
<220> FEATURE:
<223> OTHER INFORMATION: Synthesized

<400> SEQUENCE: 11

Met Glu Trp Ser Trp Val Phe Leu Phe Phe Leu Ser Val Thr Thr Gly
1               5                   10                  15

Val His Ser Gln Ala Cys Thr Glu Arg Met Ala Leu His Asn Leu Cys
            20                  25                  30

Gly Gly Gly Gln Ala Thr Glu Tyr Glu Tyr Leu Asp Tyr Asp Phe Leu
        35                  40                  45

Pro Glu Thr Glu Pro Pro Glu Gly Gly Gly Ala Gly Gly Gly Gly
    50                  55                  60

Asp Lys Thr His Thr Cys Pro Pro Cys Pro Ala Pro Glu Ala Leu Gly
65                  70                  75                  80

Ala Pro Ser Val Phe Leu Phe Pro Pro Arg Pro Arg Asp Thr Leu Met
                85                  90                  95

Ile Ser Arg Thr Pro Glu Val Thr Cys Val Val Val Asp Val Ser His
            100                 105                 110

Glu Asp Pro Glu Val Gln Phe Asn Trp Tyr Val Asp Gly Val Glu Val
        115                 120                 125

His Asn Ala Gln Thr Gln Pro Arg Glu Glu Gln Tyr Asn Ser Thr Tyr
    130                 135                 140

Arg Val Val Ser Val Leu Thr Val Leu His Gln Asp Trp Leu Asn Gly
145                 150                 155                 160

Arg Glu Tyr Arg Cys Arg Val Ser Asn Arg Ala Leu Pro Ala Pro Ile
                165                 170                 175

Glu Arg Thr Ile Ser Arg Ala Arg Gly Gln Pro Arg Glu Pro Gln Val
            180                 185                 190

Tyr Thr Leu Pro Pro Ser Arg Asp Glu Leu Thr Gln Asn Gln Val Ser
        195                 200                 205

Leu Thr Cys Leu Val Arg Gly Phe Tyr Pro Ser Asp Ile Ala Val Glu
    210                 215                 220

Trp Glu Ser Asn Gly Gln Pro Glu Asn Asn Tyr Arg Thr Thr Pro Pro
225                 230                 235                 240

Val Leu Asp Ser Asp Gly Ser Phe Phe Leu Tyr Ser Arg Leu Thr Val
                245                 250                 255

Asp Lys Ser Arg Trp Gln Gln Gly Asn Val Phe Ser Cys Ser Val Met
            260                 265                 270
```

His Glu Ala Leu His Asn His Tyr Thr Gln Arg Ser Leu Ser Leu Ser
            275                 280                 285

Pro Gly Arg
    290

<210> SEQ ID NO 12
<211> LENGTH: 264
<212> TYPE: PRT
<213> ORGANISM: Artificial Sequence
<220> FEATURE:
<223> OTHER INFORMATION: Synthesized

<400> SEQUENCE: 12

Gln Ala Thr Glu Tyr Glu Tyr Leu Asp Tyr Asp Phe Leu Pro Glu Thr
1               5                   10                  15

Glu Pro Pro Glu Arg Thr His Thr Cys Pro Cys Pro Ala Pro Glu
            20                  25                  30

Ala Leu Gly Ala Pro Ser Val Phe Leu Phe Pro Pro Arg Pro Arg Asp
            35                  40                  45

Thr Leu Met Ile Ser Arg Thr Pro Glu Val Thr Cys Val Val Val Asp
    50                  55                  60

Val Ser His Glu Asp Pro Glu Val Gln Phe Asn Trp Tyr Val Asp Gly
65                  70                  75                  80

Val Glu Val His Asn Ala Gln Thr Gln Pro Arg Glu Glu Gln Tyr Asn
                85                  90                  95

Ser Thr Tyr Arg Val Val Ser Val Leu Thr Val Cys Leu Gln Asp Trp
            100                 105                 110

Leu Asn Gly Arg Glu Tyr Arg Cys Arg Val Ser Asn Arg Ala Leu Pro
        115                 120                 125

Ala Pro Ile Glu Arg Thr Ile Ser Arg Ala Arg Gly Gln Pro Arg Glu
    130                 135                 140

Pro Gln Val Tyr Thr Leu Pro Pro Ser Arg Asp Glu Leu Thr Gln Asn
145                 150                 155                 160

Gln Val Ser Leu Thr Cys Leu Val Arg Gly Phe Tyr Pro Ser Asp Ile
                165                 170                 175

Ala Val Glu Trp Glu Ser Asn Gly Gln Pro Glu Asn Asn Tyr Arg Thr
            180                 185                 190

Thr Pro Pro Val Leu Asp Ser Asp Gly Ser Phe Phe Leu Tyr Ser Arg
        195                 200                 205

Leu Thr Val Asp Lys Ser Arg Trp Gln Gln Gly Asn Val Phe Ser Cys
    210                 215                 220

Ser Val Met His Glu Ala Leu His Asn His Tyr Thr Gln Arg Ser Leu
225                 230                 235                 240

Ser Leu Ser Pro Gly Arg Pro Thr Leu Tyr Asn Val Ser Leu Val Met
                245                 250                 255

Ser Asp Thr Ala Gly Thr Cys Tyr
            260

<210> SEQ ID NO 13
<211> LENGTH: 5
<212> TYPE: PRT
<213> ORGANISM: Artificial Sequence
<220> FEATURE:
<223> OTHER INFORMATION: Synthesized

<400> SEQUENCE: 13

Gly Ser Gly Gly Ser
1               5

```
<210> SEQ ID NO 14
<211> LENGTH: 5
<212> TYPE: PRT
<213> ORGANISM: Artificial Sequence
<220> FEATURE:
<223> OTHER INFORMATION: Synthesized

<400> SEQUENCE: 14

Gly Gly Gly Gly Ser
1               5

<210> SEQ ID NO 15
<211> LENGTH: 4
<212> TYPE: PRT
<213> ORGANISM: Artificial Sequence
<220> FEATURE:
<223> OTHER INFORMATION: Synthesized

<400> SEQUENCE: 15

Gly Gly Gly Ser
1

<210> SEQ ID NO 16
<211> LENGTH: 226
<212> TYPE: PRT
<213> ORGANISM: Artificial Sequence
<220> FEATURE:
<223> OTHER INFORMATION: Synthesized

<400> SEQUENCE: 16

Asp Arg Thr His Thr Cys Pro Pro Cys Pro Ala Pro Glu Ala Leu Gly
1               5                   10                  15

Ala Pro Ser Val Phe Leu Phe Pro Pro Arg Pro Arg Asp Thr Leu Met
                20                  25                  30

Ile Ser Arg Thr Pro Glu Val Thr Cys Val Val Val Asp Val Ser His
            35                  40                  45

Glu Asp Pro Glu Val Gln Phe Asn Trp Tyr Val Asp Gly Val Glu Val
    50                  55                  60

His Asn Ala Gln Thr Gln Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Arg Glu Tyr Arg Cys Arg Val Ser Asn Arg Ala Leu Pro Ala Pro Ile
            100                 105                 110

Glu Arg Thr Ile Ser Arg Ala Arg Gly Gln Pro Arg Glu Pro Gln Val
        115                 120                 125

Tyr Thr Leu Pro Pro Ser Arg Asp Glu Leu Thr Gln Asn Gln Val Ser
    130                 135                 140

Leu Thr Cys Leu Val Arg Gly Phe Tyr Pro Ser Asp Ile Ala Val Glu
145                 150                 155                 160

Trp Glu Ser Asn Gly Gln Pro Glu Asn Asn Tyr Arg Thr Thr Pro Pro
                165                 170                 175

Val Leu Asp Ser Asp Gly Ser Phe Phe Leu Tyr Ser Arg Leu Thr Val
            180                 185                 190

Asp Arg Ser Arg Trp Gln Gln Gly Asn Val Phe Ser Cys Ser Val Met
        195                 200                 205

His Glu Ala Leu His Asn His Tyr Thr Gln Arg Ser Leu Ser Leu Ser
    210                 215                 220

Pro Gly
225
```

```
<210> SEQ ID NO 17
<211> LENGTH: 248
<212> TYPE: PRT
<213> ORGANISM: Artificial Sequence
<220> FEATURE:
<223> OTHER INFORMATION: Synthetic

<400> SEQUENCE: 17

Asp Arg Thr His Thr Cys Pro Pro Cys Pro Ala Pro Glu Ala Leu Gly
1               5                   10                  15

Ala Pro Ser Val Phe Leu Phe Pro Pro Arg Pro Arg Asp Thr Leu Met
            20                  25                  30

Ile Ser Arg Thr Pro Glu Val Thr Cys Val Val Val Asp Val Ser His
        35                  40                  45

Glu Asp Pro Glu Val Gln Phe Asn Trp Tyr Val Asp Gly Val Glu Val
50                  55                  60

His Asn Ala Gln Thr Gln Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Arg Glu Tyr Arg Cys Arg Val Ser Asn Arg Ala Leu Pro Ala Pro Ile
            100                 105                 110

Glu Arg Thr Ile Ser Arg Ala Arg Gly Gln Pro Arg Glu Pro Gln Val
        115                 120                 125

Tyr Thr Leu Pro Pro Ser Arg Asp Glu Leu Thr Gln Asn Gln Val Ser
    130                 135                 140

Leu Thr Cys Leu Val Arg Gly Phe Tyr Pro Ser Asp Ile Ala Val Glu
145                 150                 155                 160

Trp Glu Ser Asn Gly Gln Pro Glu Asn Asn Tyr Arg Thr Thr Pro Pro
                165                 170                 175

Val Leu Asp Ser Asp Gly Ser Phe Phe Leu Tyr Ser Arg Leu Thr Val
            180                 185                 190

Asp Arg Ser Arg Trp Gln Gln Gly Asn Val Phe Ser Cys Ser Val Met
        195                 200                 205

His Glu Ala Leu His Asn His Tyr Thr Gln Arg Ser Leu Ser Leu Ser
    210                 215                 220

Pro Gly Gly Gly Gly Gln Ala Thr Glu Tyr Glu Tyr Leu Asp Tyr Asp
225                 230                 235                 240

Phe Leu Pro Glu Thr Glu Pro Pro
                245

<210> SEQ ID NO 18
<211> LENGTH: 180
<212> TYPE: PRT
<213> ORGANISM: Artificial Sequence
<220> FEATURE:
<223> OTHER INFORMATION: Synthesized

<400> SEQUENCE: 18

Gly Val Glu Val His Asn Ala Gln Thr Gln Pro Arg Glu Glu Gln Tyr
1               5                   10                  15

Asn Ser Thr Tyr Arg Val Val Ser Val Leu Thr Val Leu His Gln Asp
            20                  25                  30

Trp Leu Asn Gly Arg Glu Tyr Arg Cys Arg Val Ser Asn Arg Ala Leu
        35                  40                  45

Pro Ala Pro Ile Glu Arg Thr Ile Ser Arg Ala Arg Gly Gln Pro Arg
    50                  55                  60
```

Glu Pro Gln Val Tyr Thr Leu Pro Pro Ser Arg Asp Glu Leu Thr Gln
65                  70                  75                  80

Asn Gln Val Ser Leu Thr Cys Leu Val Arg Gly Phe Tyr Pro Ser Asp
                85                  90                  95

Ile Ala Val Glu Trp Glu Ser Asn Gly Gln Pro Glu Asn Asn Tyr Arg
            100                 105                 110

Thr Thr Pro Pro Val Leu Asp Ser Asp Gly Ser Phe Phe Leu Tyr Ser
        115                 120                 125

Arg Leu Thr Val Asp Arg Ser Arg Trp Gln Gln Gly Asn Val Phe Ser
    130                 135                 140

Cys Ser Val Met His Glu Ala Leu His Asn His Tyr Thr Gln Arg Ser
145                 150                 155                 160

Leu Ser Leu Ser Pro Gly Gly Gly Gly Cys Thr Glu Arg Met Ala Leu
                165                 170                 175

His Asn Leu Cys
            180

<210> SEQ ID NO 19
<211> LENGTH: 243
<212> TYPE: PRT
<213> ORGANISM: Artificial Sequence
<220> FEATURE:
<223> OTHER INFORMATION: Synthesized

<400> SEQUENCE: 19

Met Glu Trp Ser Trp Val Phe Leu Phe Phe Leu Ser Val Thr Thr Gly
1               5                   10                  15

Val His Ser Thr His Thr Cys Pro Pro Cys Pro Ala Pro Glu Ala Leu
            20                  25                  30

Gly Ala Pro Ser Val Phe Leu Phe Pro Pro Arg Pro Arg Asp Thr Leu
        35                  40                  45

Met Ile Ser Arg Thr Pro Glu Val Thr Cys Val Val Val Asp Val Ser
    50                  55                  60

His Glu Asp Pro Glu Val Gln Phe Asn Trp Tyr Val Asp Gly Val Glu
65                  70                  75                  80

Val His Asn Ala Gln Thr Gln Pro Arg Glu Glu Gln Tyr Asn Ser Thr
                85                  90                  95

Tyr Arg Val Val Ser Val Leu Thr Val Leu His Gln Asp Trp Leu Asn
            100                 105                 110

Gly Arg Glu Tyr Arg Cys Arg Val Ser Asn Arg Ala Leu Pro Ala Pro
        115                 120                 125

Ile Glu Arg Thr Ile Ser Arg Ala Arg Gly Gln Pro Arg Glu Pro Gln
    130                 135                 140

Val Tyr Thr Leu Pro Pro Ser Arg Asp Glu Leu Thr Gln Asn Gln Val
145                 150                 155                 160

Ser Leu Thr Cys Leu Val Arg Gly Phe Tyr Pro Ser Asp Ile Ala Val
                165                 170                 175

Glu Trp Glu Ser Asn Gly Gln Pro Glu Asn Asn Tyr Arg Thr Thr Pro
            180                 185                 190

Pro Val Leu Asp Ser Asp Gly Ser Phe Phe Leu Tyr Ser Arg Leu Thr
        195                 200                 205

Val Asp Arg Ser Arg Trp Gln Gln Gly Asn Val Phe Ser Cys Ser Val
    210                 215                 220

-continued

```
Met His Glu Ala Leu His Asn His Tyr Thr Gln Arg Ser Leu Ser Leu
225                 230                 235                 240
Ser Pro Gly
```